(12) United States Patent
Chakrapani et al.

(10) Patent No.: US 9,079,870 B2
(45) Date of Patent: Jul. 14, 2015

(54) THIOL MEDIATED/ACTIVATED PRODRUGS OF SULFUR DIOXIDE ($SO_2$) HAVING ANTI-BACTERIAL ACTIVITY

(71) Applicant: INDIAN INSTITUTE OF SCIENCE EDUCATION AND RESEARCH-PUNE, Pune (IN)

(72) Inventors: Harinath Chakrapani, Pune (IN); Satish Ramesh Malwal, Shrirampur (IN)

(73) Assignee: Indian Institute of Science Education and Research-Pune, Pune (IN)

( * ) Notice: Subject to any disclaimer, the term of this patent is extended or adjusted under 35 U.S.C. 154(b) by 0 days.

(21) Appl. No.: 13/690,842

(22) Filed: Nov. 30, 2012

(65) Prior Publication Data

US 2014/0121211 A1 May 1, 2014

(30) Foreign Application Priority Data

Oct. 31, 2012 (IN) .......................... 3162/MUM/2012

(51) Int. Cl.

| | | |
|---|---|---|
| *C07D 295/26* | (2006.01) | |
| *C07D 211/96* | (2006.01) | |
| *A61K 31/18* | (2006.01) | |
| *A61K 45/06* | (2006.01) | |
| *A61K 31/222* | (2006.01) | |
| *A61K 31/40* | (2006.01) | |
| *A61K 31/5377* | (2006.01) | |
| *A61K 31/495* | (2006.01) | |
| *A61K 31/4453* | (2006.01) | |
| *C07D 207/48* | (2006.01) | |
| *A61K 31/277* | (2006.01) | |
| *C07C 311/17* | (2006.01) | |
| *C07C 311/18* | (2006.01) | |
| *C07C 311/21* | (2006.01) | |

(52) U.S. Cl.
CPC .............. *C07D 295/26* (2013.01); *A61K 31/18* (2013.01); *A61K 31/222* (2013.01); *A61K 31/277* (2013.01); *A61K 31/40* (2013.01); *A61K 31/4453* (2013.01); *A61K 31/495* (2013.01); *A61K 31/5377* (2013.01); *A61K 45/06* (2013.01); *C07C 311/17* (2013.01); *C07C 311/18* (2013.01); *C07C 311/21* (2013.01); *C07D 207/48* (2013.01); *C07D 211/96* (2013.01)

(58) Field of Classification Search
None
See application file for complete search history.

(56) References Cited

U.S. PATENT DOCUMENTS

| | | | | |
|---|---|---|---|---|
| 6,380,429 | B1 * | 4/2002 | Smith | ............................ 564/87 |
| 2009/0163697 | A1 * | 6/2009 | Crich et al. | ................... 530/345 |

FOREIGN PATENT DOCUMENTS

WO      WO96/06838      *    3/1996

OTHER PUBLICATIONS (CAS143) Chemical Abstract Registry No. 889794-14-3, indexed in the Registry File on STN CAS Online Jun. 28, 2006.*
Malwal et al. Synthesis and antimycobacterial activity of prodrugs of sulfur dioxide (SO2). Bioorganic & Medicinal Chemistry Letter, 2012, 22, 3603-3606.*
Crich et al. One-Pot Synthesis of Dissymmetric Diamides Based on the Chemistry of Cyclic Monothioanhydrides. Scope and Limitations and Application to the Synthesis of Glycodipeptides. Journal of Organich Chemistry, 2009, 74, 3886-3893 (including supplementary information).*
Crich et al. Amino Acid and Peptide Synthesis and Functionalization by the Reaction of Thioacids with 2,4-Dinitrobenzenesulfonamides. Organic Letters, 2007, 9, 4423-4426 (including supplementary information).*
Ito et al. A medium-term rat liver bioassay for rapid in vivo detection of carcinogenic potential of chemicals. Cancer Science, 2003, 94, 3-8.*
Malwal et al. Design, Synthesis, and Evaluation of Thiol-Activated Sources of Sulfur Dioxide (SO2) as Antimycobacterial Agents. Journal of Medicinal Chemistry, 2012, 55, 553-557. (including supplemental information) (Published Nov. 30, 2011).*
Gaylord Chemical Company, LLC. Dimethyl Sulfoxide (DMSO) Health and Safety Information. Oct. 2007, p. 1-16.*
Messeri et al. A Novel Deprotection/Functionalisation Sequence using 2,4-Dintriobenzenesulfonamide: Part I. Tetrahedron Letter, 1998, 39, 1669-1672.*
Supporting information of "Malwal et al. Synthesis and antimycobacterial activity of prodrugs of sulfur dioxide (SO2). Bioorganic and Medicinal Chemistry Letter 2012, 22, 3603-3606".*
PubMed printout of "Landrigan et al. A historical study of the use of agar as a delivery vehicle for alcohol or iron to rats. Alcohol. 1989, 6, 173-178.".*

(Continued)

*Primary Examiner* — Michael Barker
*Assistant Examiner* — Po-Chih Chen
(74) *Attorney, Agent, or Firm* — Kramer Amado, P.C.

(57) ABSTRACT

Disclosed herein are thiol mediated/activated prodrugs of $SO_2$, particularly 2,4-dinitrophenylsulfonamide analogs, having Formula-I or pharmaceutically acceptable salts thereof exhibiting tunable release profiles of $SO_2$ with significant therapeutic efficacy against bacterial infections. Further, the present invention provides pharmaceutical compositions comprising compound of Formula I or pharmaceutically acceptable salts thereof, along with pharmaceutically acceptable carriers/excipients.

15 Claims, 5 Drawing Sheets

(56) References Cited

OTHER PUBLICATIONS

Ito et al., A medium-term rat liver bioassay for rapid in vivo detection of carcinogenic potential of chemicals. Cancer Science 2003, 94, 3-8.*

Chemical Abstract Registr No. 1219349-36-6, indexed in the Registry File on STN CAS Online Apr. 15, 2010.*

CAPLUS printout of "Fukuyama et al., 2,4-dinitrobenzenesulfonamide: a simple and practical method for the preparation of a variety of secondary amines and diamines, Tetrahedron Letters 1997, 38, 5831-5834.".*

Cardona et al., Extended safety studies of the attenuated live tuberculosis vaccine SO2 based on phoP mutant. Vaccine 27 (2009) 2499-2505.

Henderson, Science behind this anti-microbial, anti-oxidant, wine additive. Practical Winery & Vineyard Journal, Jan./Feb. 2009. [http://www.practicalwinery.com/janfeb09/page1.htm, viewed on Nov. 30, 2012].

Fukuyama et al., 2,4-Dinitrobenzenesulfonamides: A Simple and Practical Method for the Preparation of a Variety of Secondary Amines and Diamines. Tetrahedron Letters, vol. 38, No. 33, pp. 5831-5834, 1997.

Chen et al., Fluorescent and calorimetric probes for detection of thiols. Chem. Soc. Rev., 2010, 39, 2120-2135.

Newton et al., Distribution of Thiols in Microorganisms; Mycothiol Is a Major Thiol in Most Actinomycetes, Journal of Bacteriology, Apr. 1996, p. 1990-1995.

* cited by examiner where, 7x: 4-methoxyanilline; 7y: 2-hydroxethylthio-2,4-dinitrobenzene (a)

(b)

THIOL MEDIATED/ACTIVATED PRODRUGS OF SULFUR DIOXIDE (SO₂) HAVING ANTI-BACTERIAL ACTIVITY

CROSS-REFERENCE TO RELATED APPLICATIONS

This application claims the benefit of Indian Application No. 3162/MUM/2012, filed on Oct. 31, 2012, the entire disclosures of which is incorporated herein by reference.

TECHNICAL FIELD

The present invention relates to thiol mediated/activated prodrugs of $SO_2$, particularly 2,4-dinitrophenylsulfonamide analogues, having Formula-I or pharmaceutically acceptable salts thereof exhibiting tunable release profiles of $SO_2$ with significant therapeutic efficacy against bacterial infections. Further, the present invention provides pharmaceutical compositions comprising compound of Formula I or pharmaceutically acceptable salts thereof, along with pharmaceutically acceptable carriers/excipients.

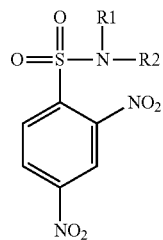

Formula-I

BACKGROUND AND PRIOR ART

The bacterial infection is caused due to the Pathogenic bacteria such as genus *Streptococcus, Staphylococcus, Mycobacterium, Helicobacter, Pseudomonas, Enterococcus, Escherichia* etc.

Among the pathogens *S. aureus* is the most common species of *staphylococcus* to cause Staph infections. The said pathogen is also referred as "golden staph" or "Oro staphira", which is Gram-positive coccal bacterium. *Staphylococcus aureus* is a part of the skin flora found in the nose and on skin. "*S. aureus*" can cause a range of illnesses from minor skin infections, such as pimples, impetigo, boils (furuncles), cellulitis folliculitis, carbuncles, scalded skin syndrome and abscesses, to life-threatening diseases such as pneumonia, meningitis, osteomyelitis, endocarditis, toxic shock syndrome (TSS), bacteremia and septicemia.

*Enterococcus faecalis* is a nonmotile, gram-positive, spherical commensal bacterium, inhabiting the gastrointestinal tracts of humans and other mammals. *E. faecalis* is listed as the first to the third leading cause of nosocomial infections which may mostly occur after surgery of the abdomen or a puncturing trauma, also due to increased use of IV's and catheters. Further it cause urinary tract infections, bacterimia, endocarditis, meningitis, and wound infections along with many other bacteria.

One of the bacterial diseases with highest disease burden is tuberculosis, caused by the bacterium *Mycobacterium tuberculosis*.

Tuberculosis causes millions of fatalities each year and in combination with HIV is proving to be a significant threat to global health. Although several new promising drug candidates are under consideration for clinical use, the increasing incidences of multi-drug resistant (MDR) and extensively drug resistant (XDR) strains of *Mycobacterium tuberculosis* (Mtb) necessitates new strategies for targeting this pathogen.

$SO_2$ is an environmental pollutant that is toxic to humans at elevated levels; chronic exposure to $SO_2$ induces oxidative stress and asthma-like symptoms. SO2 has diverse documented biological effects including damage to biomacromolecules such as proteins, lipids and DNA. Oxidation of sulfur dioxide by metal ions produces sulfur trioxide radical, which possibly mediates damage to biomacromolecules. Furthermore, sulfite, the anionic form of sulfur dioxide can break disulfide linkages to produce S-sulfonates. Thus, $SO_2$ can participate in oxidative as well as reductive processes under physiological conditions and may perturb redox equilibrium in cells. Recently, alteration of redox homeostasis in Mtb has been proposed as an effective mechanism for targeting this bacterium.

Further Pat Henderson et al. in Practical winery and vineyard Journal 02/2009 discloses broad-spectrum antimicrobial agent, sulfur dioxide, having an inhibitory effect on a wide variety of microorganisms.

Thus, sulfur dioxide may have diverse mechanisms for cytotoxicity induction and multiple biological targets. Despite such well-documented deleterious effects, $SO_2$ (in the form of bisulfite, metabisulfite and sulfite) has also been routinely used as an antibiotic and antioxidant in the food industry, in wineries and is well tolerated in most individuals. Barring certain individual cases of allergies, sulfur dioxide is well-tolerated in humans; in certain meats that are consumed on a daily basis, $SO_2$ levels can reach up to 450 mg $kg^{-1.9}$. Thus, it was envisaged that the susceptibility of bacteria to the deleterious effects of SO2 could be exploited to develop new SO2-based tuberculosis drug candidates. To tap its therapeutic potential and possibly to avoid undesirable side effects, controlled delivery of SO2 is necessary.

The poor bioavailability of gaseous sulfur dioxide precludes its usage for therapeutic purposes and the use of complex inorganic sulfite mixtures, typically used to generate $SO_2$ in biological systems, suffers from a lack of control of rate and amount of $SO_2$ generated. As there were no reliable $SO_2$ sources available, the present inventors proposed to develop organic donors of sulfur dioxide with tunable release profiles in order to evaluate their efficacy as against bacterial infections.

It has been reported in Tetrahedron Letters 38, (33), 1997, 5831-5834 by Fukuyama et al. that amines can be protected by the reaction with 2,4-dinitrophenylsulfonyl chloride (DNsCl) as 2,4-dinitrophenylsulfonamides, wherein deprotection of such amides was carried out by thiols such as 2-mercaptoacetic acid in basic medium to produce amines in good yields (cf below scheme), wherein a byproduct of these deprotection reactions was sulfur dioxide.

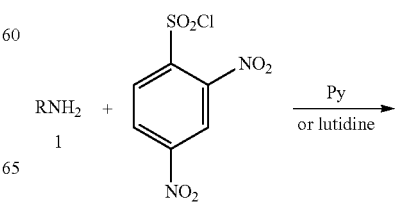

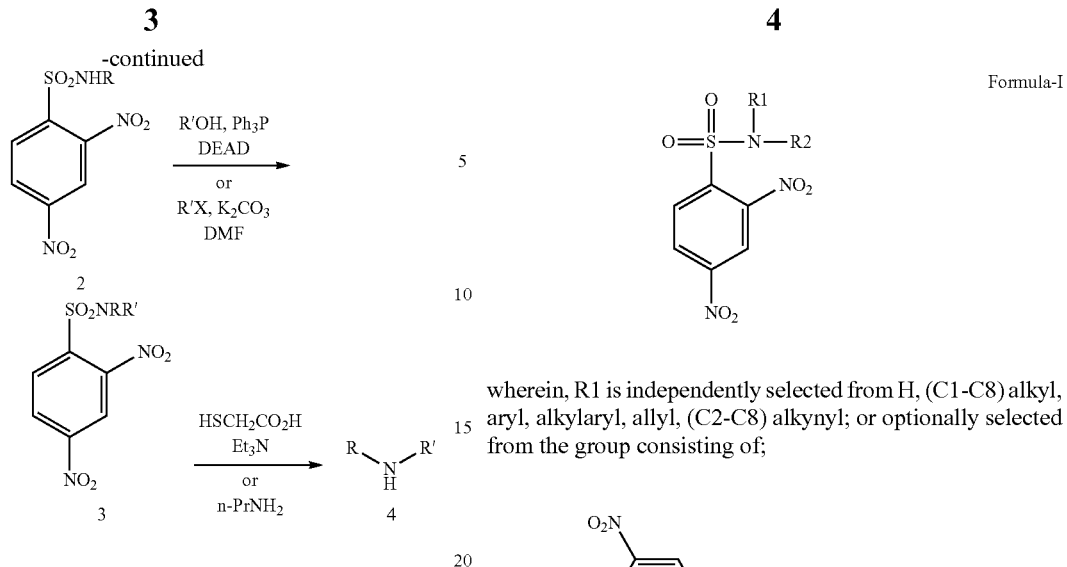

-continued 2 3 4

Though, the release of $SO_2$ from the deprotection of 2,4-dinitrophenylsulfonamides is known from the above article, the thiol activated 2,4-dinitrophenylsulfonamides analogs as source of $SO_2$ with tunable release profile which significantly inhibits the growth of bacterial infection is not yet reported.

2,4-Dinitrophenylsulfonamides have also been used in thiol detection systems for environmental and biological applications.

Xiaoqiang Chen et al. in Chem. Soc. Rev., 2010, (39), 2120-2135 focuses on the fluorescent or colorimetric sensors for thiols according to their unique mechanisms between sensors and thiols, including cleavage of sulfonamide and sulfonate ester by thiols, cleavage of disulfide by thiols, wherein the thiols are selected from cysteine, homocysteine and glutathione.

Furthermore, variation of the groups on the amine may provide a handle for modulating SO2 release profiles. Unlike mammalian cells, Mtb does not contain glutathione (GSH) but mycothiol (MSH) as the primary thiol in millimolar concentrations.

Gerald L. Newton et al. in Journal of bacteriology, vol. 178, no. 7 Apr. 1996, 1990-1995 discloses that MSH production is confined to actinomycetes and shows that mycobacteria, including *Mycobacterium tuberculosis*, produce high levels of thiol (MSH).

MSH is critical for the maintenance of redox homeostasis and alteration of thiol-levels could induce stress to Mtb. Upon reaction with a 2,4-dinitrophenylsulfonamide, MSH is expected to be arylated to generate sulfur dioxide intracellularly. Thus this two-pronged strategy of introduction of $SO_2$ and a thiol-depleting agent could inhibit Mtb growth.

Therefore the present inventors have developed organic donors/prodrugs of SO2, i.e. 2,4-dinitrobenzenesulfonamides analogues with tunable release profiles of $SO_2$ in order to evaluate their therapeutic efficacy against bacterial infections which remains objective of the present invention.

SUMMARY OF THE INVENTION

In accordance with the objective, the present invention provides thiol mediated/activated reliable prodrugs of $SO_2$ having general Formula-I, which exhibits tunable release profiles of $SO_2$ with significant therapeutic efficacy against bacterial infections.

Formula-I wherein, R1 is independently selected from H, (C1-C8) alkyl, aryl, alkylaryl, allyl, (C2-C8) alkynyl; or optionally selected from the group consisting of;

or

R2 represents group consisting of allyl or;

or wherein, (n) is either 0 or 1;

R3 is independently selected from H, halogen, —CF3, (C1-C6) alkoxy, —CN, wherein R4 and R4' are identical or independently selected from the group consisting of H, substituted or unsubstituted (C1-C6) alkyl; and R1 and R2 together form substituted or unsubstituted 5 or 6 membered heterocyclic ring, optionally containing substituted or unsubstituted heteroatom such as O or N, wherein substituents are selected from the group consisting of H, (C1-C6) alkyl, —COO(R5); where R5 is selected from H, (C1-C6) alkyl.

In an aspect, the present invention relates to a pharmaceutical composition comprising an effective amount of active ingredient compound of Formula I or as its salts along with pharmaceutically acceptable excipients for treating bacterial infections.

In yet another aspect, the invention provides method of treating bacterial infections in a mammal comprising administering an effective amount of compound of formula I or its pharmaceutical salt in association with one or more pharmaceutical carriers.

The bacterial infections according to the invention may be caused due to gram negative, gram positive and *Mycobacterium tuberculosis*.

In yet another aspect, the invention provides use of compounds of formula I or its pharmaceutical salt optionally in association with one or more pharmaceutical carriers for the treatment of bacterial infections in a mammal.

DETAILED DESCRIPTION OF INVENTION

Figure 1A:
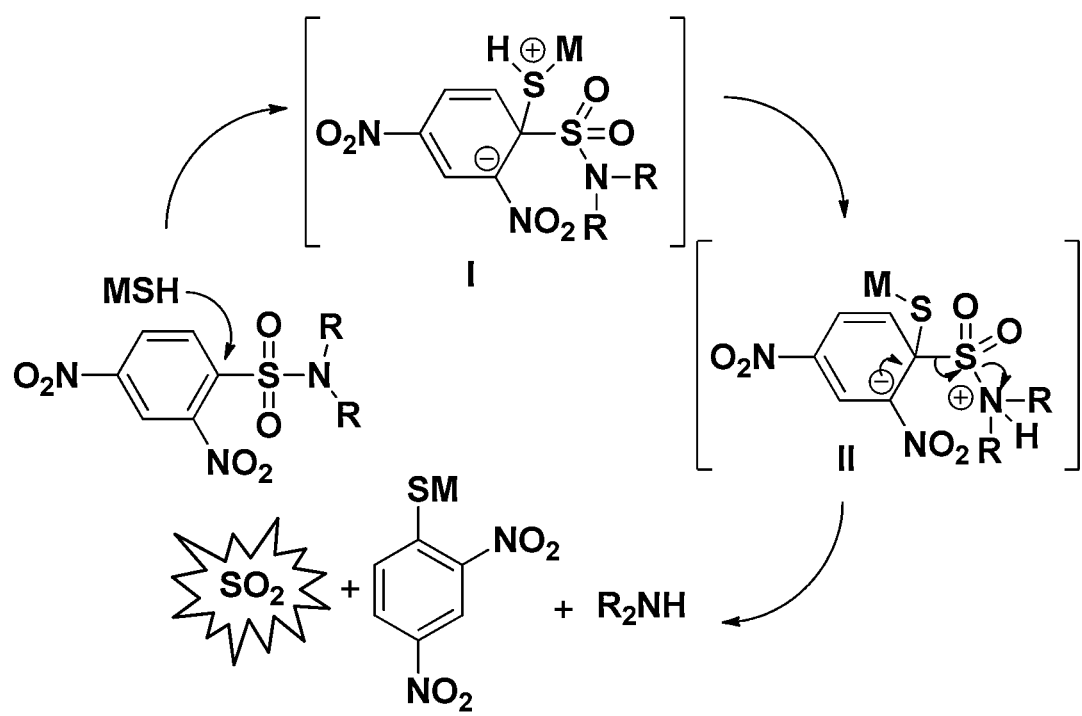
FIG. 1(a) depicts plausible mechanism for thiol mediated decomposition of to generate $SO_2$ from compounds such as (1)

The invention will now be described in detail in connection with certain preferred and optional embodiments, so that various aspects thereof may be more fully understood and appreciated.

The present invention provides thiol mediated/activated reliable prodrugs of $SO_2$ having general Formula-I or pharmaceutically acceptable salts thereof, which exhibits tunable release profile of SO2 with significant therapeutic efficacy against bacterial infections.

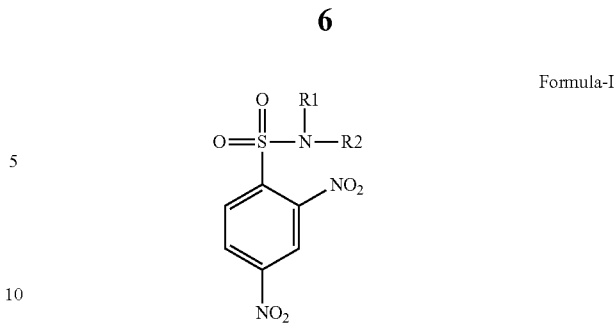

Formula-I wherein, R1 is independently selected from H, (C1-C8) alkyl, aryl, arylalkyl, allyl, (C2-C8) alkynyl; or optionally selected from the group consisting of;

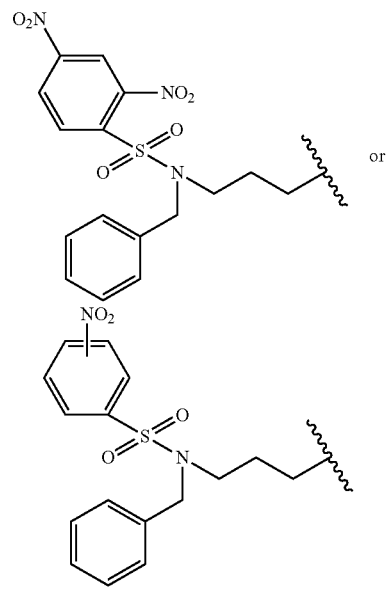

R2 represents group consisting of allyl, or

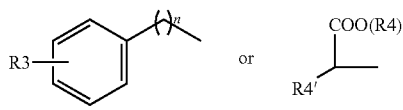

wherein, (n) is either 0 or 1;
R3 is independently selected from H, halogen, —$CF_3$, (C1-C6) alkoxy, —CN,
wherein R4 and R4' are identical or independently selected from the group consisting of H, substituted or unsubstituted (C1-C6) alkyl; and
R1 and R2 together form substituted or unsubstituted 5 or 6 membered heterocyclic ring, optionally containing substituted or unsubstituted heteroatom such as O or N, wherein substituents are selected from the group consisting of H, (C1-C6) alkyl, —COO(R5); where R5 is selected from H, (C1-C6) alkyl.

The term "alkyl" includes all straight chain and branched alkyl selected from the group methyl, ethyl, n-propyl, iso-propyl, n-butyl, sec-butyl, iso-butyl, t-butyl, n-pentyl and n-hexyl and like thereof.

The term "alkoxy" includes the group selected from methoxy, ethoxy, propoxy, butoxy and like thereof.

The terms 'halogen' and 'halo' include fluorine, chlorine, bromine and iodine, and fluoro, chloro, bromo and iodo, respectively.

The compounds of the present invention may contain one or more asymmetric carbon atoms and may exist in racemic and optically active form.

2,4-dinitrophenylsulfonyl group of Formula I of present invention, also represented as "DNs"

In an embodiment, the present invention relates to synthesis of 2,4-dinitrosulfonamide analogues (Formula-I) which can be prepared by the process known in the art, wherein the process comprises reaction of corresponding amine with 2,4-dinitrophenylsulfonyl chloride (DNsCl); whereas the alkylated derivatives of compounds of Formula I, can be prepared by treatment of corresponding alkyl halide with suitable 2,4-dinitrosulfonamide under suitable condition.

The thiol used according to the instant invention is particularly cysteine, therefore in preferred embodiment the present invention provides cysteine mediated/activated reliable prodrugs of $SO_2$ having general Formula-I, or pharmaceutically acceptable salts thereof, which exhibit tunable release profile of $SO_2$ with significant therapeutic efficacy against bacterial infections.

A large number of prodrugs of $SO_2$ having Formula I, which are synthesized by the process mentioned hereinabove, are disclosed in below Table 1.

TABLE 1

| Sr. No. | Compound | R1 | R2 | R3 | R4 |
|---|---|---|---|---|---|
| 1. | 1 | H | benzyl | — | — |
| 2. | 2 | H | benzyl | 4-methoxy | — |
| 3. | 3 | H | benzyl | 4-chloro | — |
| 4. | 4 | H | benzyl | 4-$CF_3$ | — |
| 5. | 5 | H | benzyl | 2-$CF_3$ | — |
| 6. | 6 | H | phenyl | — | — |
| 7. | 7 | H | phenyl | 4-methoxy | — |
| 8. | 8 | H | phenyl | 2-methoxy | — |
| 9. | 9 | H | phenyl | 3-fluoro | — |
| 10. | 10 | H | phenyl | 4-fluoro | — |
| 11. | 11 | H | phenyl | 4-CN | — |
| 12. | 12 | H | (S) N-(1-phenylethyl)- | — | — |
| 13. | 13 | H | (R) N-(1-phenylethyl)- | — | — |
| 14. | 14 | H | 2-phenylethyl | — | — |
| 15. | 15 | Methyl | benzyl | — | — |
|  | 16 | n-propyl |  |  |  |
|  | 17 | Phenyl |  |  |  |
| 16. | 18 | Methyl | phenyl | — | — |
| 17. | 19 | Methyl | 2-phenylethyl | — | — |
|  | 20 | benzyl |  |  |  |
| 18. | 21 | H | COO(R4) on CH with R4' | — | R4 and R4' = methyl |
| 19. | 22 | \[pyrrolidine N-DNs with $CO_2R5$, $R5$ = methyl\] | | — | — |
| 20. | 23 | \[morpholine-type ring with DNs, X = O\] | | — | — |
|  | 24 | \[piperidine ring with DNs, X = $CH_2$\] | | — | — |
|  | 25 | \[piperazine ring with DNs, X = N-Methyl\] | | — | — |

$$DNs-N(R1)-R2 \quad \longrightarrow \quad \text{Formula -I}$$

TABLE 1-continued

| Sr. No. | Compound | R1 | R2 | R3 | R4 |
|---|---|---|---|---|---|
| 21. | 32 | R1 = allyl | R2 = allyl | — | — |
| 22. | 33 | R1 = propynyl or propargyl | R2 = benzyl | — | — |
| 23. | 34 | ![structure: 2,4-dinitrophenylsulfonyl-N-benzyl-N-butyl] | benzyl | — | — |
| 24. | 35 | ![structure: 2,4-dinitrophenylsulfonyl-N-benzyl-N-butyl] | phenyl | 2-methoxy | — |
| 25. | 36 | ![structure: 2,4-dinitrophenylsulfonyl-N-benzyl-N-butyl] | phenyl | 3-methoxy | — |
| 26. | 37 | ![structure: 2,4-dinitrophenylsulfonyl-N-benzyl-N-butyl] | phenyl | 4-methoxy | — |

TABLE 1-continued

| Sr. No. | Compound | R1 | R2 | R3 | R4 |
|---|---|---|---|---|---|
| 27. | 38 | (2,4-dinitrophenyl-SO2-N(CH2Ph)-(CH2)3-) | phenyl | — | — |
| 28. | 39 | (2,4-dinitrophenyl-SO2-N(CH2Ph)-(CH2)3-) | phenyl | 2-Fluoro | — |
| 29. | 40 | (2-nitrophenyl-SO2-N(CH2Ph)-(CH2)3-) | benzyl | — | — |
| 30. | 41 | (3-nitrophenyl-SO2-N(CH2Ph)-(CH2)3-) | benzyl | — | — |

TABLE 1-continued

| Sr. No. | Compound | R1 | R2 | R3 | R4 |
|---|---|---|---|---|---|
| 31. | 42 | O$_2$N-(structure shown) | benzyl | — | — |

In accordance with Table 1, the thiol activated prodrugs of SO$_2$ having Formula I of instant invention, encompasses the following compounds;
i. N-benzyl-2,4-dinitrophenylsulfonamide (1);
ii. N-(4-methoxybenzyl)2,4-dinitrophenylsulfonamide (2);
iii. N-(4-chlorobenzyl)2,4-dinitrophenylsulfonamide (3);
iv. N-(4-trifluoromethyl benzyl) 2,4-dinitrophenylsulfonamide (4);
v. N-(2-trifluoromethyl benzyl) 2,4-dinitrophenylsulfonamide (5);
vi. N-phenyl, 2,4-dinitrophenylsulfonamide (6);
vii. N-(4-methoxyphenyl) 2,4-dinitrophenylsulfonamide (7);
viii. N-(2-methoxyphenyl) 2,4-dinitrophenylsulfonamide (8);
ix. N-(3-fluorophenyl) 2,4-dinitrophenylsulfonamide (9);
x. N-(4-fluorophenyl) 2,4-dinitrophenylsulfonamide (10);
xi. N-(4-cyanophenyl) 2,4-dinitrophenylsulfonamide (11);
xii. (S) N-(1-phenylethyl)-2,4-dinitrobenzenesulfonamide (12);
xiii. (R) N-(1-phenylethyl)-2,4-dinitrobenzenesulfonamide (13);
xiv. N-(2-phenylethyl) 2,4-dinitrophenylsulfonamide (14);
xv. (N-benzyl, N-methyl) 2,4-dinitrophenylsulfonamide (15);
xvi. (N-benzyl, N-propyl) 2,4-dinitrophenylsulfonamide (16);
xvii. (N-benzyl, N-phenyl) 2,4-dinitrophenylsulfonamide (17);
xviii. (N-methyl, N-phenyl) 2,4-dinitrophenylsulfonamide (18);
xix. N-methyl, N-(2-phenylethyl) 2,4-dinitrophenylsulfonamide (19);
xx. N-benzyl, N-(2-phenylethyl) 2,4-dinitrophenylsulfonamide (20);
xxi. Methyl 2-{[(2,4-dinitrophenyl)sulfonyl]amino}propanoate (21);
xxii. Methyl 1[(2,4-dinitrophenyl)sulfonyl]pyrrolidine-2-carboxylate (22);
xxiii. 4-[(2,4-dinitrophenyl)sulfonyl]morpholine (23);
xxiv. 1-[(2,4-dinitrophenyl)sulfonyl]piperidine (24);
xxv. 1-[(2,4-dinitrophenyl)sulfonyl]-4-methylpiperazine (25);
xxvi. N,N-diallyl-2,4-dinitrobenzenesulfonamide (32);
xxvii. N-benzyl-2,4-dinitro-N-prop-2-yn-1-ylbenzenesulfonamide (33);
xxviii. N,N'-(propane-1,3-diyl)bis(N-benzyl-2,4-dinitrobenzenesulfonamide) (34);
xxix. N-benzyl-N-(3-(N-(2-methoxyphenyl)-2,4-dinitrophenylsulfonamido)propyl)-2,4-dinitrobenzenesulfonamide (35);
xxx. N-benzyl-N-(3-(N-(3-methoxyphenyl)-2,4-dinitrophenylsulfonamido)propyl)-2,4-dinitrobenzenesulfonamide (36);
xxxi. N-benzyl-N-(3-(N-(4-methoxyphenyl)-2,4-dinitrophenylsulfonamido)propyl)-2,4-dinitrobenzenesulfonamide (37);
xxxii. N-benzyl-N-(3-(2,4-dinitro-(N-phenyl) phenylsulfonamido)propyl)-2,4 dinitro benzene sulfonamide (38);
xxxiii. N-benzyl-N-(3-(N-(2-fluorophenyl)-2,4-dinitrophenylsulfonamido)propyl)-2,4-dinitro
xxxiv. benzenesulfonamide (39);
xxxv. N-benzyl-N-(3-(N-benzyl-2-nitrophenylsulfonamido) propyl)-2,4-dinitrobenzenesulfon-amide (40);
xxxvi. N-benzyl-N-(3-(N-benzyl-3-nitrophenylsulfonamido)propyl)-2,4-dinitrobenzenesulfon-amide (41);
xxxvii. N-benzyl-N-(3-(N-benzyl-4-nitrophenylsulfonamido)propyl)-2,4-dinitrobenzenesulfon-amide (42);

In an another embodiment, the compounds of the present invention are characterized by spectral analysis such as NMR, CNMR, IR, Mass and UV, elemental analysis and melting point etc.

Also the 2,4-dinitrophenylsulfonamide analogues of Formula I, are well characterized by the known chromatographic techniques like HPLC, GC, TLC etc.

According to another preferred embodiment, the compounds of formula I are tested for its antibacterial activity by reacting with thiols.

The antibacterial activity of compounds of Formula I against the growth of gram positive bacteria such as S. aureus and E. feacalis is represented in (Table 2a).

One such study of the invention includes Mtb inhibitory activity. In the instant study, the generation of SO$_2$, particularly the yield of SO2 after commencement of the reaction with cysteine with compounds of 2,4-dinitrophenylsulfonamide analogues (Formula I) and their antimycobacterial activity, (Mtb inhibitory activity) is given below in Table 2b.

The SO$_2$ analysis during thiol mediated decomposition and antimycobacterial activity of 2,4 dinitrosulfonamides and related analogues is demonstrated below in Table 3.

In yet another embodiment the invention provides compounds of Formula I, which comprises more than one SO$_2$ moiety to generate high percentage release of SO$_2$/mol after commencement of the reaction with thiol and thereby enhance the antibacterial activity of the said compounds. The release profile of compounds having more than one SO$_2$ moiety is given below in Table 5.

Further the present invention discloses that among the 2,4 dinitrobenzylsulfonamide analogue compounds of Formula I, the compound (1) i.e. N-benzyl-2-4-dinitrophenylsulfonamide produces nearly 100% yield of SO$_2$ in 30 min after commencement of the reaction of compound (1) with cysteine, which strongly inhibits Mtb growth (MIC about 0.05 µg/ml) (cf Table 2b).

In another embodiment, cysteine-mediated decomposition of compounds of the Formula I or its salts generated elevated levels of $SO_2$ in 30 minutes (≥75%) with MICs in the range of 0.05 to >100 µg/ml.

In another embodiment, the present invention provides a pharmaceutical composition comprising of the active ingredient of Formula I or its pharmaceutically acceptable salts, along with pharmaceutically acceptable excipients or carriers, for the treatment of antibacterial infections in a mammal. Generally, the quantity of active compound will range between 0.5% to 90% by weight of the composition. Normally, the effective amount of dosage of antibacterial active component will be in the range of about 0.1 to about 100 mg/kg, more preferably about 3.0 mg to about 50 mg/kg of body weight/day.

The quantity of the compound of formula I used in pharmaceutical compositions of the present invention will vary depending upon the body weight of the patient and the mode of administration and can be of any effective amount to achieve the desired therapeutic effect. The compound of the present invention can also be administered optionally with other antibacterial actives depending on the disease conditions. The additional antibacterial active compound may be selected from the group consisting of Fluoroquinolones, Cephalosporins, Penicillins, Carbepenems, Aminoglycosides, Tetracyclines etc.

Further the synergistic antimycobacterial effect of instant pharmaceutical composition can be achieved in combination with additional known anti-tuberculosis drugs selected from the group consisting of rifampin, isoniazide, ethambutol, pyrazinamide etc. The pharmaceutical composition according to the invention can be in the form of a solid such as, pills, powders, granules, tablets, capsules, pellets, beads etc. or can be present in the liquid form such as solutions, emulsions, suspensions, syrup etc. or can be used in the form of inhalants or Parenteral injection.

According to the invention, the pharmaceutical compositions containing compounds of Formula-I may be administered using any effective amount, any form of pharmaceutical composition and any route of administration effective for the treatment of tuberculosis. After formulation with an appropriate pharmaceutically acceptable carrier in a desired dosage, as known by those of skill in the art, the pharmaceutical compositions of present invention can be administered by any means that delivers the active pharmaceutical ingredient (s) to the site of the body whereby it can exert a therapeutic effect on the patient.

The excipients or carriers are selected from inert diluents such as dextrose, sugar, sorbitol, mannitol, polyvinylpyrrolidone, disintegrants such as starch, Crosslinked polymers, binders such as sucrose, lactose; starches, cellulose or modified cellulose such as microcrystalline cellulose, hydroxypropyl cellulose (HPC); xylitol, sorbitol or maltitol; gelatin; polyvinylpyrrolidone (PVP), polyethylene glycol (PEG), lubricants such as magnesium stearate or talc and/or agents for achieving a depot effect such as carboxypolymethylene, carboxymethyl-cellulose, cellulose acetate phthalate or polyvinyl acetate, coatings layer such as polyvinylpyrrolidone or shellac, gum arabic, talc, titanium oxide or sugar.

Solutions or suspensions containing the compounds of the general formula I according to the invention can additionally comprise taste-enhancing agents such as saccharin, cyclamate or sugar and other flavourings. They can moreover comprise suspending excipients or preservatives.

In yet another embodiment, the invention provides method of treating or inhibiting the growth of bacterial infections in a subject comprising administering an effective amount of compound of formula I or its pharmaceutical salt in association with one or more pharmaceutical carriers.

The bacterial infections according to the invention may be caused due to gram negative, gram positive such as *S. aureus, E. feacalis* and *Mycobacterium tuberculosis*.

In a specific embodiment, the invention provides methods of inhibiting the growth of *Mycobacterium tuberculosis* $H_{37}R_v$ strain which comprises administering an effective amount of compound of Formula I or its pharmaceutical salt in association with one or more pharmaceutical carriers.

In yet another embodiment, the invention provides use of compounds of formula I or its pharmaceutical salt optionally in association with one or more pharmaceutical carriers for the treatment of bacterial infections in a subject.

Accordingly, the invention provides the use of the compounds of Formula I to inhibit the growth of bacterial infections caused due to pathogens selected from the group consisting of *Staphylococcus, Enterococcus* and *Mycobacterium* particularly *Mycobacterium tuberculosis* (Mtb) $H_{37}R_v$ strain (Table 2a, 2b and 3).

The subject as described in above embodiment is a mammal.

The following examples, which include preferred embodiments, will serve to illustrate the practice of this invention, it being understood that the particulars shown are by way of examples and for purpose of illustrative discussion of preferred embodiments of the invention only and are not limiting the scope of the invention.

Experimental

The preliminary results of instant invention indicated that the rate of $SO_2$ generation affected inhibitory activity of 2,4-dinitrophenylsulfonamide related compounds.

The antibacterial activity of thiol mediated/activated prodrugs of SO2 i.e. 2,4-dinitrophenylsulfonamide related compounds against the gram positive pathogenic bacteria selected from the group *S. aureus, E. feacalis* is given herein below Table 2a.

TABLE 2a

| Sr. No | Compound | Structure | MIC (µg/mL) S. aureus ATCC 29213 | MIC (µg/mL) E. feacalis ATCC 29212 |
|---|---|---|---|---|
| 1. | 2 | 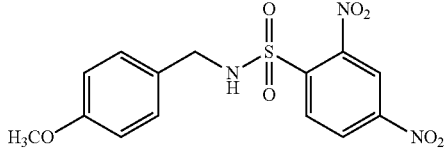 [SMILES: COc1ccc(CNS(=O)(=O)c2ccc([N+](=O)[O-])cc2[N+](=O)[O-])cc1] | >16 | >16 |

TABLE 2a-continued

| Sr. No | Compound | Structure | MIC (μg/mL) S. aureus ATCC 29213 | MIC (μg/mL) E. feacalis ATCC 29212 |
|---|---|---|---|---|
| 2. | 32 | 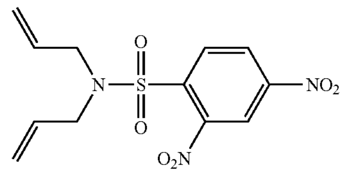 [SMILES: C=CCN(CC=C)S(=O)(=O)c1ccc([N+](=O)[O-])cc1[N+](=O)[O-]] | 8 | >16 |
| 3. | 33 | 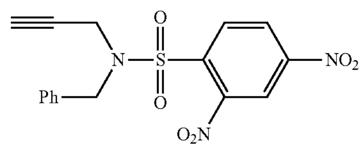 | 4 | 8 |
| 4. | 11 | 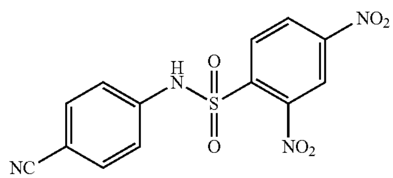 [SMILES: N#Cc1ccc(NS(=O)(=O)c2ccc([N+](=O)[O-])cc2[N+](=O)[O-])cc1] | >16 | >16 |
| 5. | 10 | 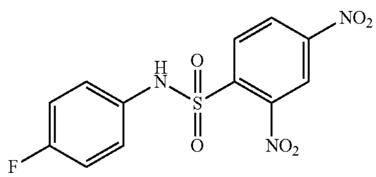 [SMILES: O=[N+]([O-])c1ccc(S(=O)(=O)Nc2ccc(F)cc2)c([N+](=O)[O-])c1] | 16 | >16 |
| 6. | 7 | 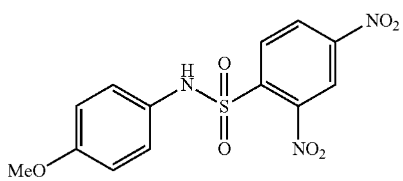 [SMILES: COc1ccc(NS(=O)(=O)c2ccc([N+](=O)[O-])cc2[N+](=O)[O-])cc1] | >16 | >16 |
| 7. | 1 | 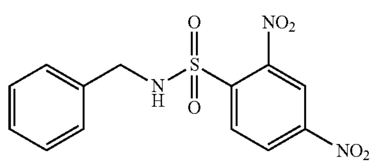 [SMILES: O=[N+]([O-])c1ccc(S(=O)(=O)NCc2ccccc2)c([N+](=O)[O-])c1] | >16 | >16 |
| 8. | 8 | 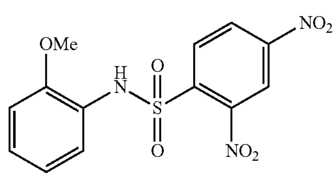 [SMILES: COc1ccccc1NS(=O)(=O)c1ccc([N+](=O)[O-])cc1[N+](=O)[O-]] | 8 | 16 |
| 9. | 15 | 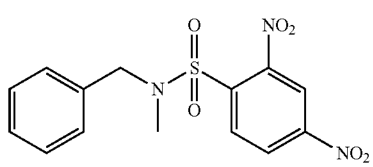 [SMILES: CN(Cc1ccccc1)S(=O)(=O)c1ccc([N+](=O)[O-])cc1[N+](=O)[O-]] | 8 | >16 |
| 10. | 24 | 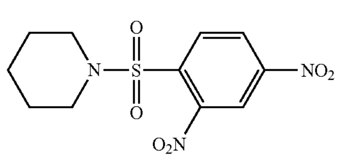 [SMILES: O=[N+]([O-])c1ccc(S(=O)(=O)N2CCCCC2)c([N+](=O)[O-])c1] | 4 | >16 |

In accordance with Table 2a the Minimum inhibitory concentration (MIC) of prodrugs of $SO_2$ having Formula I to inhibit growth of bacterial infections caused due to pathogens like *S. aureus* and *E. feacalis* were found >16 g/mL.

The inventors demonstrated that small modifications to the structure of the amine resulted in a significant change in the half-lives of SO2 generation (t1/2=2 to 63 min) Thus, varying the amine structure could potentially help modulate anti-*mycobacterial* activity. In order to study the effects of varying sterics and/or electronics on chemical and biological properties, analogues with comparable clogPs to compound (1) were synthesized by process known in the art.

The calculated partition coefficients (clogP) of thiol-mediated prodrugs of sulfur dioxide (Formula I), yield of $SO_2$ and anti-*mycobacterial* activities of specific compounds of Formula I is represented in Table 2b.

ment of the reaction with cysteine (10 equiv). $SO_2$ was determined as sulfite in pH 7.4 using an ion chromatograph equipped with a conductivity-based detector. Under such reaction conditions, the benzylamine derivative (1) produced 100% $SO_2$ in 30 min (Table 2b, entry 1). Presence of an electron withdrawing or electron donating group did not significantly affect the yield of $SO_2$ in comparison with (1) (Table 2b, entries 2-5). The sulfanilide (6) produced 55 µM (55% yield) $SO_2$ under comparable reaction conditions (Table 2b, entry 6). Amongst the aniline derivatives, inventors found a strong electronic effect on the yield of sulfur dioxide during decomposition of aniline derivatives, wherein the presence of an electron donating group enhanced the yield of $SO_2$ in comparison with aniline (Table 2b, entries 7 and 8). Conversely, when an electron withdrawing group is present on the aromatic ring of aniline, the yield of $SO_2$ decreased in comparison with aniline (Table 2b, entries 9-11). The effect TABLE 2b

| Entry | Compound | Mol. Wt. | Yield[a] (%) | C logP[b] | $SO_2$ yield, 30 min (µM)[c] | $SO_2$ yield, 5 min (µM)[c] | pKaH[d] | MIC (µg/mL) | MIC (µM) |
|---|---|---|---|---|---|---|---|---|---|
| 1 | 1 | 337.05 | 41 | 2.87 | 100 | 83 | 9.51 | 0.05 | 0.15 |
| 2 | 2 | 367.33 | 33 | 2.78 | 84 | 74 | 9.50 | 0.25 | 0.68 |
| 3 | 3 | 371.75 | 54 | 3.58 | 96 | 77 | 9.44 | 0.4 | 1.07 |
| 4 | 4 | 405.31 | 43 | 3.75 | 75 | 79 | 9.45 | 0.4 | 0.98 |
| 5 | 5 | 405.31 | 54 | 3.75 | 84 | 81 | 9.23 | 1.56 | 3.84 |
| 6 | 6 | 323.28 | 30 | 2.76 | 55 | 37 | 4.64 | 3.13 | 9.69 |
| 7 | 7 | 353.30 | 66 | 2.69 | 80 | 39 | 5.11 | 1.56 | 4.4 |
| 8 | 8 | 353.30 | 70 | 2.69 | 86 | 57 | 4.42 | 3.13 | 8.85 |
| 9 | 9 | 341.27 | 70 | 2.93 | 24 | 5 | 3.22 | 25f | 73 |
| 10 | 10 | 341.27 | 48 | 2.92 | 55 | 18 | 3.80 | 6.25 | 18.31 |
| 11 | 11 | 348.29 | 47 | 2.24 | 5 | 6 | 1.63 | >50 | >100 |
| 12 | 12 | 351.33 | 47 | 3.17 | 97 | 80 | 9.73 | 1.56 | 4.44 |
| 13 | 13 | 351.33 | 38 | 3.17 | 94 | 78 | 9.73 | 1.56 | 4.44 |
| 14 | 14 | 351.33 | 79 | 3.19 | 100 | 76 | 9.79 | 0.4 | 1.13 |
| 15 | 15 | 351.33 | 86 | 2.41 | 100 | 79 | 9.70 | 0.4 | 1.10 |
| 16 | 16 | 379.38 | 73 | 3.47 | 96 | 68 | 9.90 | 3.13 | 8.25 |
| 17 | 17 | 413.40 | 47 | 3.87 | 94 | 44 | 3.92 | 1.56 | 4.44 |
| 18 | 18 | 337.31 | 81 | 2.10 | 94 | 89 | 5.64 | 0.78 | 2.31 |
| 19 | 19 | 365.56 | 95 | 2.74 | 84 | 79 | 10.13 | 0.78 | 2.13 |
| 20 | 20 | 441.46 | 80 | 4.50 | 75 | 37 | 9.88 | 3.13 | 7.09 |
| 21 | Isoniazide | 137.13 | — | −0.66 | — | — | — | 0.05 | 0.37 |
| 22 | Ethambutol | 204.31 | — | 2.08 | — | — | — | 1.56 | 7.63 |
| 23 | Pyrizinamide | 123.11 | — | −0.67 | — | — | — | 6.25 | 50.8 |

[a]Yield is for reaction of the amine with 2,4-dinitrophenylsulfonyl chloride or alkylation of 2,4-dinitrophenylsulfonamide.
[b]Calculated using Chembiodraw Ultra.
[c]Sulfur dioxide as sulfite was quantified using an ion chromatograph equipped with a conductivity detector: yields are 5 min and 30 min after treatment of compound (100 1M) with 10 equiv of cysteine in pH 7.4 phosphate buffer.
[d]Values are for the corresponding amine and were calculated using Marvinsketch 5.7.1.
[e]Minimum inhibitory concentration (MIC) is the minimum concentration of the compound required to inhibit 99% of bacterial growth and was found against *Mycobacterium* tuberculosis H37Rv strain.

Accordingly the inventors were prepared the benzylamine analogues 2-5 (Table 2b, entries 2-5) with electron donating and electron withdrawing groups using a previously reported method of reaction of the corresponding amine with 2,4-dinitrophenylsulfonyl chloride (DNsCl).

Similarly, aniline derivatives 6-11 were prepared using the aforementioned procedure with substituents capable of perturbing the electronics of the amine (Table 2b, entries 6-11).

In order to study the effect of changing sterics around the nitrogen bearing the DNs group, compound 12 and 13 with an alpha-methyl substituent were prepared (Table 2b, entries 12-13). The 1-phenyl-2-aminoethyl derivative 14 was prepared by treatment of the corresponding amine with DNsCl (Table 2b, entry 14), whereas the alkylated derivatives 15-20 were prepared by treating the corresponding alkyl halide with a suitable 2,4-dinitrosulfonamide (Table 2b, entries 15-20).

Further the present inventors were evaluated cysteine-mediated SO2 yields from the library of said compounds (Table 2b) by recording the yield of $SO_2$ 30 min after commencewas particularly strong in the presence of a 4-cyano group (11), whose sulfur dioxide yield (30 min) was 5% (Table 2b, entry 11). In the presence of an additional alkyl, aryl, or methylene group, either comparable or slightly diminished yield of SO2 in comparison with compound (1) was observed (Table 2b, entries 12-20).

The ability of compounds of Formula I to inhibit *Mycobacterium tuberculosis* ($H_{37}R_v$) growth was evaluated using a reported protocol. The inventors found minimum inhibitory concentrations (MICs) ranged from 0.05 to >100 mg/mL (Table 2b). While compound (1) was still most potent Mtb inhibitor in series of compounds of Formula I (Table 2b), several derivatives (2-4), (14), (15), (18) and (19) had potent Mtb inhibitory activities with MICs<1 mg/mL (Table 2b, entries 2-4, 14,15, 18 and 19);

The N-benzyl-2,4-dinitrophenylsulfonamide (1), (Table 2b) with a MIC of 0.05 µg/mL (0.15 µM), is better than those of clinically used tuberculosis drugs such as isoniazid, ethambutol and pyrazinamide, which were evaluated under similar assay conditions (Table 2b, entries 21, 22 and 23).

Figure 2:
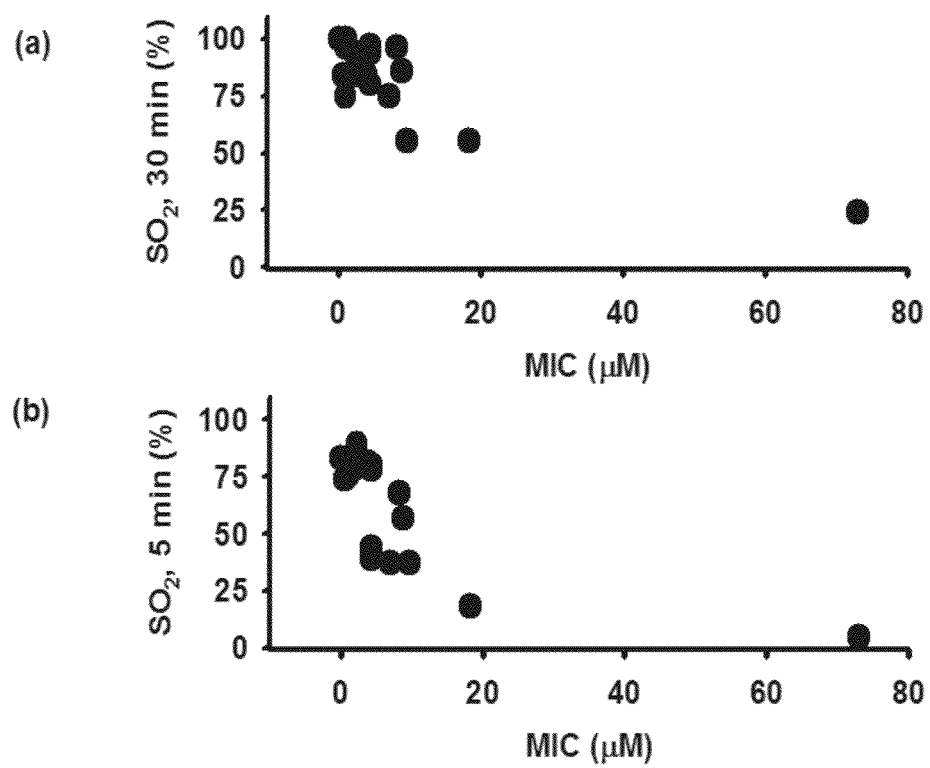
FIG. 2 depicts Relationship between sulfur dioxide yield generated during cysteine-mediated decomposition of selected 2,4-dinitrophenylsulfonamides prepared in this study and their Mtb inhibitory activity. (a) $SO_2$ yield was after 30 min; Spearman rank correlation analysis of $SO_2$ yield and MIC gave a Spearman correlation coefficient of −0.50 (P-value=0.01). (b) $SO_2$ yield was after 5 min; Spearman rank correlation analysis of $SO_2$ yield and MIC gave p=−0.69 (P-value=0.001).
Figure 3:
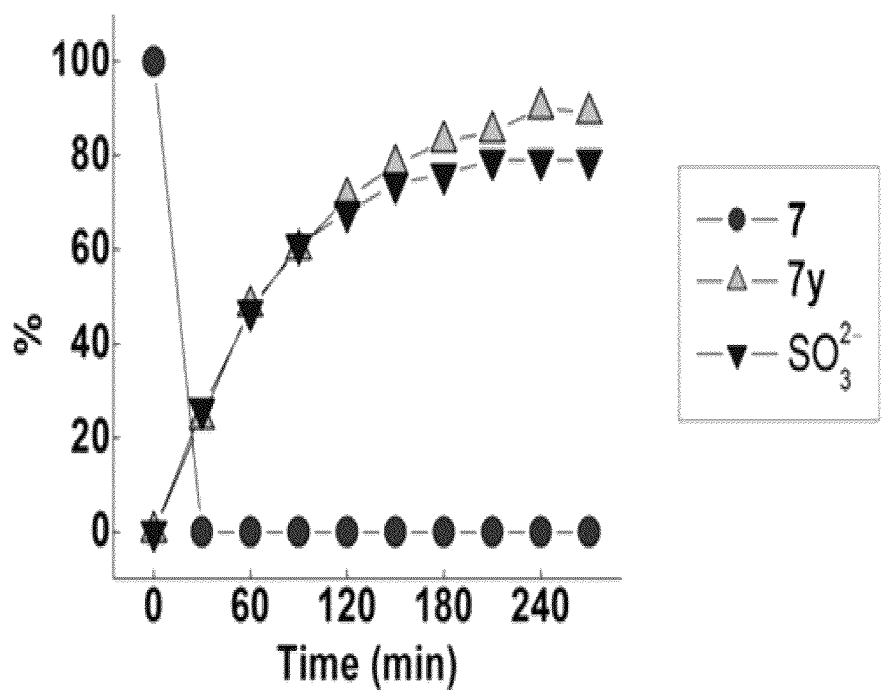
FIG. 3 depicts kinetics of decomposition of compound (7) to produce sulfur dioxide and 2-hydroxyethylthio-2,4-dinitrobenzene (7y), where disappearance of compound (7) and appearance of (7y) was followed by HPLC analysis. Production of sulfite was monitored by ion chromatography analysis. Curve fitting afforded first order rate constant for: appearance of (7y) as 0.011 $min^{-1}$; and appearance of sulfite as 0.014 $min^{-1}$.

In accordance with FIG. 2, the data analysis revealed that the most potent Mtb inhibitors generated elevated levels of $SO_2$ in 30 min (≥75% yield). Spearman rank correlation analysis of MICs with sulfur dioxide yields (FIG. 2a) revealed a moderate negative correlation value of Spearman rank correlation coefficient p=−0.50 (P-value=0.02) between MICs and SO2 yields. Similar data collected for SO2 yields after 5 min (Table 2b), however, correlated well with MICs (FIG. 2b) p=−0.69 (P-value=0.001). Such results indicate a role for efficiency of SO2 generation, which in turn is related to reactivity of the compound with thiols, in the observed Mtb inhibitory activity of series of compounds of Formula I.

In accordance with (Chart 1) 2,4-dinitrophenylsulfonamides 21-25 and 1 of primary and secondary amines were prepared by known process. To study the effect of increasing sterics on the nitrogen bearing the sulfonamide on its reactivity toward thiols, N-methyl (15) and N-propyl (16) derivatives were prepared by alkylation of (1), whereas to study the effect of electronic modulation of the aromatic ring attached to the DNs group on the rate of SO2 generation, aniline derivatives (6), (7), (9) were prepared by the reaction of the corresponding amine with DNsCl. Additionally, to study the effect of removal of one or both the aryl nitro groups and replacement of the aryl ring with a methyl group, compounds 26 to 29 were prepared by the known method in the art.

Chart: 1

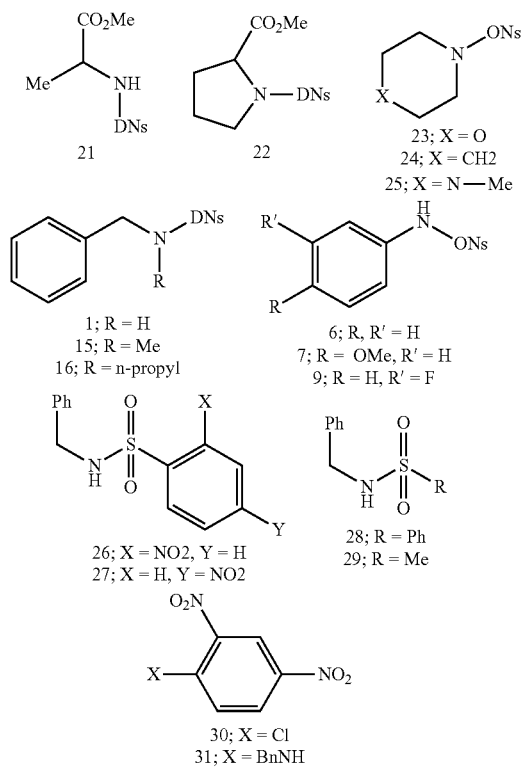

$SO_2$ from environmental and biological samples is typically quantified by estimation of sulfite, the anionic form of $SO_2$ in basic media (eq 1).

equv-1

The present inventors were used an ion chromatograph (IC) equipped with a conductivity detector for quantitative $SO_2$ analysis as sulfite. Further cysteine-mediated decomposition of compounds of (Table 3 entries 1-15) in pH 7.4 buffer was carried out, where all 2,4-dinitrosulfonamides (100 µM) tested were found to generate sulfite (24-100 µM) in 30 min.

The derivatives 26 and 27, which had one nitro group on the aryl ring, did not produce any detectable levels of $SO_2$ even after 4 h and neither did the analogues 28 and 29 (Table 3, entries 12-15).

Further the compounds of (Table 3, entries 1 to 15) were screened for their antimycobacterial activity against *Mycobacterium tuberculosis* $H_{37}R_v$ and minimum inhibitory concentrations (MICs) were determined.

In accordance with Table 3, eight compounds were found to have MICs<10 µg mL-1 (Table 3, entries 1,3,4,6 to 10). The compounds 21-25, 1, 15, 16, 6, 7 and 9 which all produced $SO_2$ upon reaction with cysteine, were found to have greater inhibitory activity (MIC≤25 µg mL-1) than compound 26 to 29 that were unreactive to cysteine (MIC>50 µg mL-1, Table 3, entries 12-15). The results as disclosed in Table 3 clearly indicate a correlation between the analogue's ability to release sulfur dioxide within 30 min and its Mtb inhibitory potency.

The efficient Mtb inhibitor in the series of compounds of Formula I was the benzylamine derivative i.e compound (1) with MIC of 0.05 µg mL$^{-1}$ (0.15 µM), which was better than the MIC of isoniazid (0.05 µg mL$^{-1}$ (0.37 µM) determined under similar conditions. Hence, further studies conducted were focused on understanding the mechanisms of efficacy of compound (1). Upon reaction with a number of biologically relevant nucleophiles such as amino acids and nucleosides in pH 7.4 buffer, a nearly quantitative recovery of compound (1) was observed (HPLC analysis), which was selectively reactive to thiols under physiological pH.

The present inventors also showed the thiol-selectivity of compounds of Formula-I under biologically relevant conditions. Accordingly the decomposition of 1 in the presence of thiols generated sulfur dioxide, benzylamine, and the arylated thiol. Benzylamine, a decomposition product of (1) did not show a significant inhibition of growth of Mtb at 100 µg mL-1 (Table 3, entry 16); a similar observation for N-methylbenzylamine was recorded (Table 3, entry 17), and sodium sulfite was inactive against Mtb at 100 µg mL$^{-1}$. To understand if combinations of decomposition products were responsible for Mtb inhibitory activity, a mixture of cysteine and compound (1) in pH 7.4 buffer approximately 2 h post mixing was tested at 2 µg mL$^{-1}$; the said mixture was found to be inactive against Mtb.

In view of above it was demonstrated that sulfur dioxide ($SO_2$) formation (and not sulfite) intracellularly contributes to the Mtb inhibitory activity of compound (1).

TABLE 3

SO2 analysis during Thiol-Mediated Decomposition, and Antimycobacterial Activity of 2,4-dinitrosulfonamides and Related Analogues (compounds of chart 1)

| Entry | Compound | SO2 source[a] | SO$_2$ yield, 30 min (μM)[b] | MIC (μg/mL)[c] | MIC (μM) |
|---|---|---|---|---|---|
| 1 | 21 | yes | 93 | 6.25 | 18.7 |
| 2 | 22 | yes | 83 | 12.5 | 35 |
| 3 | 23 | yes | 96 | 6.25 | 19.6 |
| 4 | 24 | yes | 91 | 0.78 | 2.5 |
| 5 | 25 | yes | 88 | 12.5 | 38 |
| 6 | 1 | yes | 100 | 0.05 | 0.15 |
| 7 | 15 | yes | 100 | 0.4 | 1.1 |
| 8 | 16 | yes | 96 | 3.13 | 8.25 |
| 9 | 6 | yes | 55 | 3.13 | 9.7 |
| 10 | 7 | yes | 79.5 | 1.56 | 4.4 |
| 11 | 9 | yes | 24 | 25 | 73 |
| 12 | 26 | no | 0 | >50 | >100 |
| 13 | 27 | no | 0 | >50 | >100 |
| 14 | 28 | no | 0 | >50 | >100 |
| 15 | 29 | no | 0 | >50 | >100 |
| 16 | BnNH$_2$ | no | — | >100 | >250 |
| 17 | BnNHMe | no | — | >100 | >250 |
| 18 | 31 | no | 0 | >100 | >250 |
| 19 | isoniazide | no | — | 0.05 | 0.37 |

[a]Sulfur dioxide was detected using a pararosaniline-based colorimetric assay.
[b]Sulfur dioxide as sulfite was quantified using an ion chromatograph equipped with a conductivity detector: yields are 30 min after treatment of compound (100 μM) with 10 equiv of cysteine in pH 7.4 phosphate buffer.
[c]Minimum inhibitory concentration (MIC) is the minimum concentration of the compound required to inhibit 99% of bacterial growth and was found against *Mycobacterium tuberculosis* H37Rv strain.

The above data clearly showed the potential of SO$_2$ to inhibit Mtb growth. Further, to study the effect of rate of SO$_2$ generation on the Mtb inhibitory activity, the time courses of cysteine-mediated SO$_2$ generation from compounds 1, 15, 16, 6, 7 and 9 which have comparable estimated cell permeability (−clogP, Table 4), were determined and compared with their antimycobacterial activities.

TABLE 4

| Entry | Compound | −clog P[a] | K (min$^{-1}$)[b] | t$_{1/2\,(min)}$[c] | Max SO2 yield (μM)[d] | pK$_{aH}$[e] |
|---|---|---|---|---|---|---|
| 1 | 1 | 2.87 | f | 2g | 100 | 9.34 |
| 2 | 15 | 2.41 | f | 4g | 100 | 9.58 |
| 3 | 16 | 3.47 | 0.1517 | 4.6 | 96 | 9.68 |
| 4 | 6 | 2.76 | 0.0273 | 25 | 94 | 4.64 |
| 5 | 7 | 2.69 | 0.0575 | 12 | 97 | 5.29 |
| 6 | 9 | 2.93 | 0.0106 | 63 | 86 | 3.38 |

[a]Calculated using Chembiodraw Ultra.
[b]Rate analysis of sulfite release from the compound (100 μM) in the presence of cysteine (10 equiv) in pH 7.4 phosphate buffer (20 mM).
[c]Half-life was estimated from rate constants.
[d]Maximum amount of sulfur dioxide generated the during the reaction with no further increase in total sulfur dioxide; values reported are a sum of sulfite and sulfate (minor, see Supporting Information).
HPLC analysis showed complete disappearance of 2,4-dinitrophenylsulfonamide.
[e]Values are for the amine without a DNs group.
[f]Accurate rate constant could not be determined.
[g]Approximate half-life estimated based on yields of sulfur dioxide.

In accordance with Table 4, the compounds tested were found to be excellent sources of SO$_2$ with maximum yields of SO$_2$ ranging from 86 to 100 μM. For compound 1 and 15, under the assay conditions, accurate determination of rate constant (k) for SO$_2$ formation was not possible; the t$_{1/2}$, for compound 1 was estimated to be 2 min; and for compound 15, t$_{1/2}$ was 4 min SO2 release during cysteine-mediated decomposition of 16, 6, 7 and 9 followed pseudo-first-order kinetics with half-lives ranging from 4.6 to 63 min.

The compounds having more than one SO$_2$ moiety wherein the percentage of SO2 release (after 30 mints) is more than the single SO2 moiety compound, per mole of compound as shown Table 5.

TABLE 5

| Compound | Structure | % SO2 (30 min) |
|---|---|---|
| 34 | (structure shown) | 152% |
| 35 | (structure shown) | 161% |

TABLE 5-continued

| Compound | Structure | % SO2 (30 min) |
|---|---|---|
| 36 | 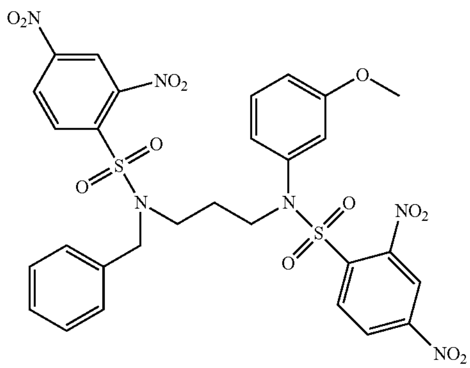 [SMILES: COc1cccc(N(CCCN(Cc2ccccc2)S(=O)(=O)c2ccc([N+](=O)[O-])cc2[N+](=O)[O-])S(=O)(=O)c2ccc([N+](=O)[O-])cc2[N+](=O)[O-])c1] | 184% |
| 37 | 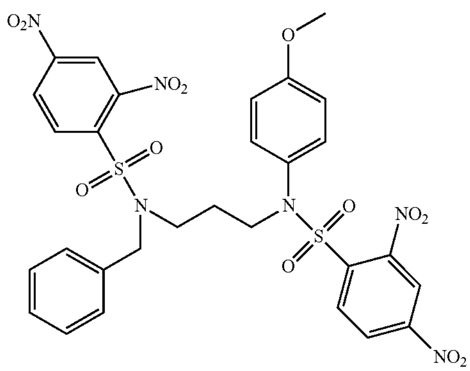 [SMILES: COc1ccc(N(CCCN(Cc2ccccc2)S(=O)(=O)c2ccc([N+](=O)[O-])cc2[N+](=O)[O-])S(=O)(=O)c2ccc([N+](=O)[O-])cc2[N+](=O)[O-])cc1] | 183% |
| 38 | 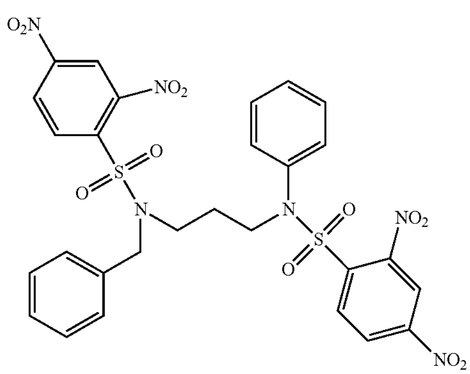 [SMILES: O=[N+]([O-])c1ccc(S(=O)(=O)N(CCCN(c2ccccc2)S(=O)(=O)c2ccc([N+](=O)[O-])cc2[N+](=O)[O-])Cc2ccccc2)c([N+](=O)[O-])c1] | 160% |
| 39 | 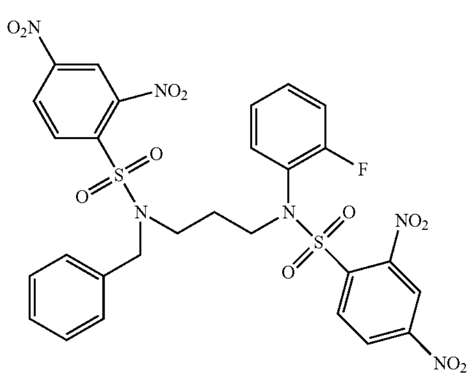 [SMILES: O=[N+]([O-])c1ccc(S(=O)(=O)N(CCCN(c2ccccc2F)S(=O)(=O)c2ccc([N+](=O)[O-])cc2[N+](=O)[O-])Cc2ccccc2)c([N+](=O)[O-])c1] | 141% |

TABLE 5-continued

| Compound | Structure | % SO2 (30 min) |
|---|---|---|
| 40 | 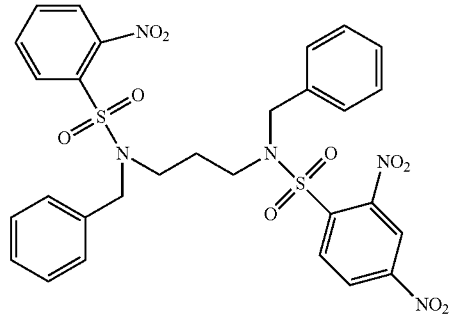 [SMILES: O=[N+]([O-])c1ccc(S(=O)(=O)N(CCCN(Cc2ccccc2)S(=O)(=O)c2ccccc2[N+](=O)[O-])Cc2ccccc2)c([N+](=O)[O-])c1] | 88% |
| 41 | 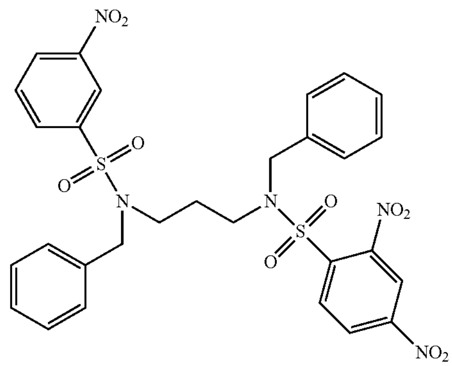 [SMILES: O=[N+]([O-])c1cccc(S(=O)(=O)N(CCCN(Cc2ccccc2)S(=O)(=O)c2ccc([N+](=O)[O-])cc2[N+](=O)[O-])Cc2ccccc2)c1] | 99% |
| 42 | 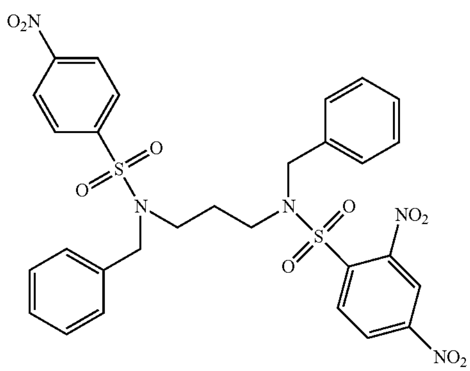 [SMILES: O=[N+]([O-])c1ccc(S(=O)(=O)N(CCCN(Cc2ccccc2)S(=O)(=O)c2ccc([N+](=O)[O-])cc2[N+](=O)[O-])Cc2ccccc2)cc1] | 98% |

In accordance with Table 5, the % of SO2 release of compounds comprising more than one $SO_2$ moiety, after commencement of the reaction with thiol (30 mints) were found ≥88%.

The plausible mechanism of decomposition of compounds of Formula I, (compound 1) is represented in FIG. 1a, wherein the thiol attack on the 2,4-dinitrophenylsulfonamide produced intermediate I, which was converted to intermediate II by a proton transfer that subsequently gave $SO_2$. It was observed that the rate constant for $SO_2$ generation (k) was depend on the stability of the transition state leading to the formation of the protonated amine intermediate II. Hence, the stronger the basicity (or weaker the conjugate acid), the greater would be the tendency of nitrogen bearing the 2,4-dinitrophenylsulfonyl group to get protonated and leave as the amine resulting in a higher k.

Further the step of protonation is rate determining step in the said mechanism. As basicity data for 2,4-dinitrosulfonamides was unavailable, the inventors compared the $pK_{aHs}$ of benzylamine, N-alkylbenzylamines, aniline, 4-methoxyaniline, and 3-fluoroaniline, with the k for their corresponding DNs derivative (Table 4, entries 1-6).

With regard to the proposed mechanism (FIG. 1a), a comparison of k and $pK_{aHs}$ revealed that an increased amine $pK_{aH}$ resulted in higher rates of $SO_2$ release. A comparison of estimated half-life of $SO_2$ generation ($t_{1/2}$) and MICs showed that the fluoro derivative 9, which was the longest among the compounds tested, was also the least potent of the 2,4-dinitrophenylsulfonamides that evaluated in the instant study (Table 3). Further analysis of data for, compounds 1, 15, 16, 6, 7 and 9 which have comparable –clogP values, showed that a higher rate of SO2 generation (k) correlated well with improved inhibitory activity.

Therefore the instant study provides a rational basis for further design of analogues of compound (1) with anti-*mycobacterial* activity. However, without data pertinent to drug uptake of 2,4-dinitrophenylsulfonamide compounds in Mtb, it is not possible to attribute differences in MICs of compounds 1, 15, 16, 6, 7 and 9 only to differences in rates of cysteine-mediated $SO_2$ generation from said compounds.

Further to test the selectivity of $SO_2$ inhibitory activity toward Mtb, a cell viability assay was conducted using human embryonic kidney 293 cells (HEK) cell lines and the IC50 for compound (1) was determined as 7 μM. Based on the MIC and IC50, compound (1) was nearly 50-fold selective in inhibitory activity (SI=47) toward Mtb over human embryonic kidney cells.

In addition to generation of SO2, the reaction of compound (1) with thiols could also affect cellular redox balance by mycothiol depletion in Mtb. The possible role of thiol-depletion in the observed efficacy of compound (1) was determined by testing the analogue of compound (1) without a sulfonyl group 31 (Chart 1), which is unreactive with thiols showed no Mtb inhibitory activity (Table 3, entry 19). These results support a role for thiol depletion and perhaps protein S-arylation as a contributor to the observed antibacterial activity of compound (1).

In view of above, the inventors provide evidence for the utility of masked sources of sulfur dioxide as antimycobacterial agents and whose Mtb inhibitory activity in part depended on the rate of thiol-mediated sulfur dioxide generation. Consequently, a major impediment to development of new drugs for infectious diseases is the cost of multistep synthesis to prepare potential drug candidates. The compounds prepared in this study can be obtained in one step from relatively inexpensive commercial sources, making them especially attractive for further development as potential drug candidates.

Figure 1B:
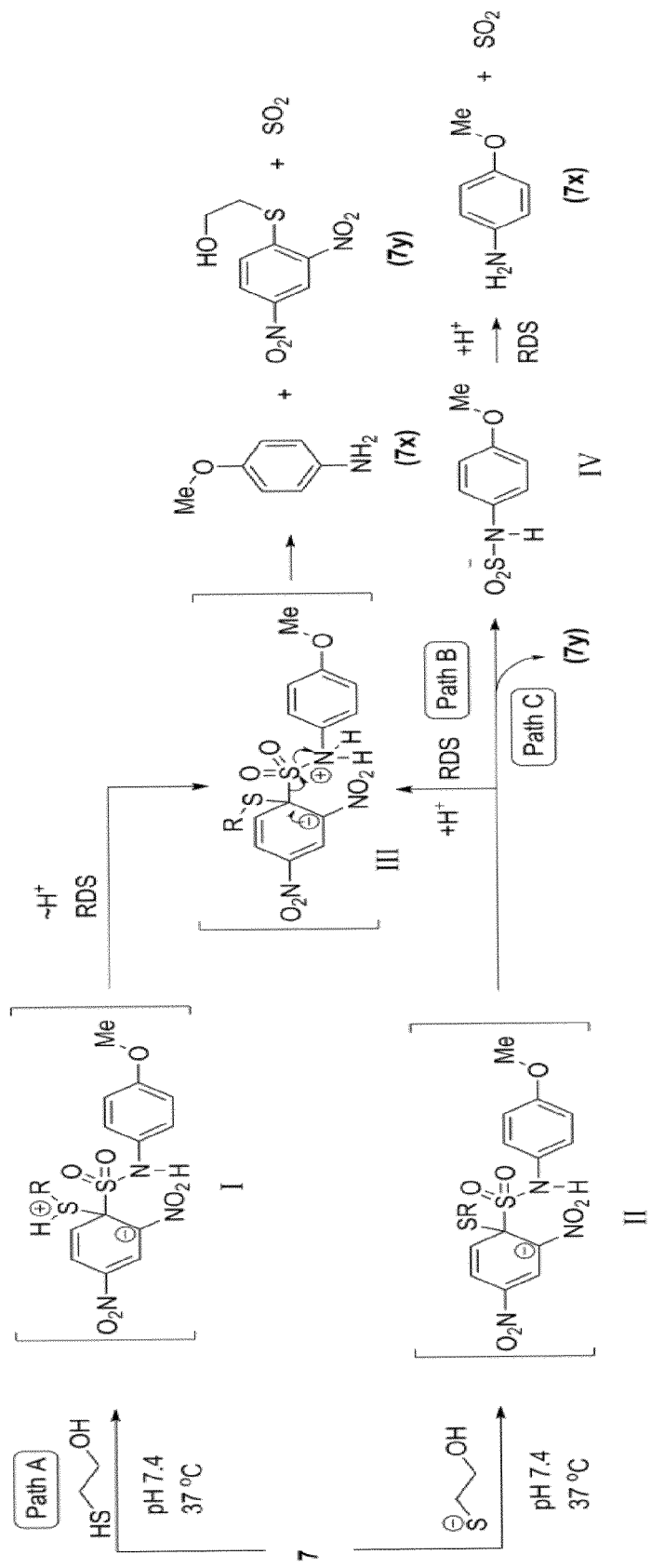
FIG. 1(b) depicts plausible mechanism for thiol mediated decomposition of to generate $SO_2$ from compound (7).

Alternatively, a detailed kinetic analysis of thiol-mediated decomposition and sulfite generation from compound (7) is represented in FIG. 1b, wherein compound (7) decomposed to simultaneously produce sulfur dioxide, and by-products like 4-methoxyaniline (7x) and 2-hydroxyethylthio-2,4-dinitrobenzene (7y). Further the rate determining step in the said mechanism was the step of protonation (either through proton transfer or addition of proton).

Figure 4:
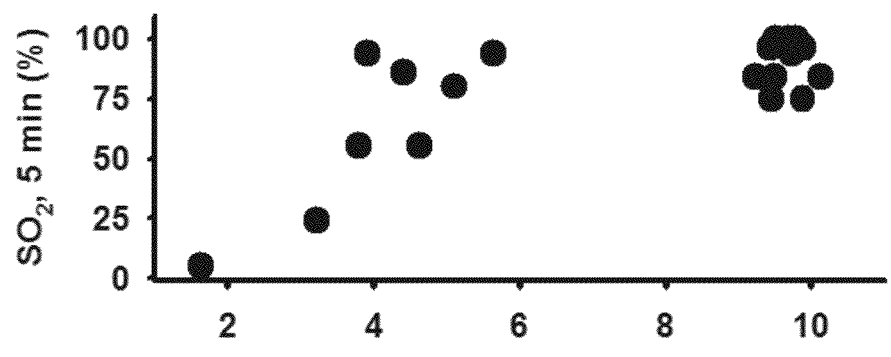
FIG. 4 depicts relationship between sulfur dioxide generated during cysteine-mediated decomposition of selected 2,4-dinitrophenylsulfonamides prepared in this study and $pK_{aH}$ of the amine from which the corresponding sulfonamide was prepared. (a) $SO_2$ yield was after 5 min; Pearson correlation analysis of $SO_2$ yield and $pK_{aH}$ gave a correlation coefficient ρ=−0.79 (P-value<0.001) (b) $SO_2$ yield was after 30 min; Pearson correlation analysis of $SO_2$ yield and $pK_{aH}$ gave a correlation coefficient r=−0.71 (P-value<0.0001).
Figure 4:
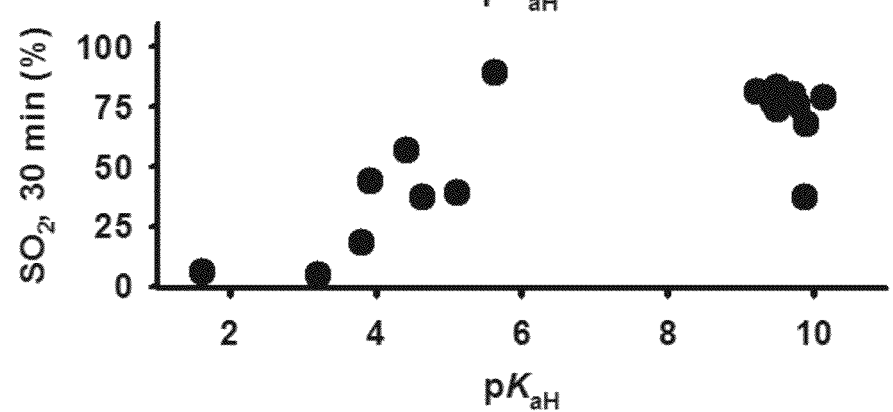

Further the inventors found a good positive correlation r=0.79 (P-value<0.0001) between $pK_{aH}$ of the amine and SO2 yields (5 min) and r=0.71 (P-value<0.001) for SO2 yields (30 min) during cysteine-mediated decomposition of 2,4-dinitrosulfonamides supporting that the proposed mechanism of formation of protonated intermediate as the rate determining step could be a general mechanism of thiol-mediated SO2 generation from 2,4-dinitrophenylsulfonamides (FIG. 4).

As a majority of the potent Mtb inhibitors in the instant study were completely decomposed in 30 min, it is perhaps less likely that they would stay unreacted, especially in the presence of (estimated) millimolar concentration of mycothiols in Mtb.

It is found that anti-mycobacterial activity of closely related structural analogues of compound of Formula I of present invention with comparable clogPs correlated well with the analogue's ability to generate sulfur dioxide upon treatment with cysteine.

In view of above, the inventors provide evidence for the utility of masked sources of sulfur dioxide as antimycobacterial agents and whose Mtb inhibitory activity in part depended on the rate of thiol-mediated sulfur dioxide generation. Consequently, a major impediment to development of new drugs for infectious diseases is the cost of multistep synthesis to prepare potential drug candidates. The compounds prepared in this study can be obtained in one step from relatively inexpensive commercial sources, making them especially attractive for further development as potential drug candidates.

The invention will now be illustrated with help of examples. The aforementioned embodiments and below mentioned examples are for illustrative purpose and are not meant to limit the scope of the invention. Various modifications of aforementioned embodiments and below mentioned examples are readily apparent to a person skilled in the art. All such modifications may be construed to fall within the scope and limit of this invention as defined by the appended claims.

EXAMPLES

Example 1

General Procedure for the Synthesis of 2,4-Dinitrophenylsulfonamides

A solution of the amine in DCM containing triethylamine or pyridine was treated with a solution of DNsCl in DCM at 0 or −40° C. The reaction mixture was warmed to RT. Work up included extraction with DCM or EtOAc followed by silica gel chromatography using mixtures of PE/EtOAc or DCM as the eluent to produce the desired compound as a yellow solid (unless otherwise stated).

Example 2

General Procedure for the Synthesis of alkylated derivatives of 2,4-Dinitrophenylsulfonamides To a solution of the 2,4-dinitrophenylsulfonamide in DMF, $K_2CO_3$ (2 eq.) and alkyl halide (2 eq.) were added at RT and reaction mixture was stirred for 2 h. The reaction was quenched with water and extracted with EtOAc. The organic layer was dried on $Na_2SO_4$ and concentrated under reduced pressure to get crude product, which was purified by silica gel column chromatography using mixtures of petroleum ether/EtOAc or DCM as the eluent to get desired compound as a yellow solid (unless otherwise stated).

Example 3

Cysteine-Activated Sulfur Dioxide Release

P-Rosaniline assay for sulfur dioxide: The dye was prepared using a literature procedure. Assay conditions: 900 μL of p-rosaniline-based dye was mixed with 50 μL of satd $HgCl_2$ solution and 50 μL of 0.2 mM sulfite. The obtained solution was covered with aluminum foil for 15 min until violet color developed and the absorbance was measured. A similar protocol was used for compounds which were treated with 10 equiv. cysteine in pH 7.4 phosphate buffer containing 1-5% DMSO (or ethanol).

Ion chromatography analysis: An ion chromatograph attached with a conductivity detector was used for sulfite analysis. One mM $NaHCO_3$/3.2 mM $Na_2CO_3$ was the eluant, and the flow rate was 0.7 mL/min Using stock solutions of sulfite, a calibration curve was generated (R2=0.9999). To 3 mL of 1 mM stock solution of compound in acetonitrile, 24 mL of phosphate buffer (pH=7.4, 20 mM) was added and vortexed for 20 s. To this mixture, 3 mL of 10 mM cysteine solution (pH 7.4) was added, and the reaction mixture was stirred at RT under inert atmosphere. Aliquots at appropriate time intervals were analyzed by IC. Maximum sulfur dioxide yield was calculated based on completion of the reaction with no further increase in sulfite formation. In all such cases, when sulfur dioxide reached a maximum, HPLC analysis of the reaction mixture showed complete disappearance of the 2,4-dinitrophenylsulfonamide.

Example 4

Antimycobacterial Activity Assay

Ten-fold serial dilutions of each test compound/drug were prepared and incorporated into Middlebrook 7H11 agar medium with OADC growth supplement. Inoculum of *Mycobacterium tuberculosis* $H_{37}R_v$ were prepared from fresh Middlebrook 7H11 agar slants with OADC growth supplement adjusted to 1 mg mL-1 (wet weight) in Tween 80 (0.05%) saline diluted to $10^{-2}$ to give a concentration of approximately 107 cfu $mL^{-1}$. Five μL of bacterial suspension was spotted into 7H11 agar tubes containing 10-fold serial dilutions of drugs per mL. The tubes were incubated at 37° C., and final readings were recorded after 28 days. The minimum inhibitory concentration (MIC) is defined as the minimum concentration of compound required to completely inhibit the bacterial growth.

Example 5

Safety data of the byproducts like amino and nitro compounds

The LD50 of amine byproduct in an Oral Rat model was found as 552 mg/kg and therefore, the amine byproducts are non-toxic in humans.

The thiolated-2,4-dinitrophenyl compound as a byproduct has been tested in an animal model and found to be relatively non-toxic and hence the same are non-toxic in humans.

Example 6

Pharmaceutical Composition

| | |
|---|---|
| Compound of formula 1 | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

General Procedure for Preparation of Pharmaceutical Composition:

The mannitol was dissolved in water; subsequently pharmaceutically acceptable colour and flavour were added to the maniitol wherein the water was evaporated to adsorb color and flavor on mannitol. Further compound of Formula I and diluent i.e. magnesium stearate were mixed together to derive at suitable dosage form such as tablet, capsule, powder.

Suitable colours, flavours and pharmaceutical excipients may be selected from the ones known in the art to prepare suitable dosage forms for conventional modes of administrations.

Example 7

Spectral Data and Characterization of the Array of 2,4-dinitrophenylsulfonamide Analogous (Compounds of Formula I)

The characterization of the compounds of Formula I is performed by using FT-IR spectrometer and melting point apparatus; whereas spectral analysis include $^1H$ and $^{13}C$ NMR spectrometer in DMSO-$d_6$ solvents. Further the mass spectra are taken on high resolution mass spectroscopy HRMS (ESI-TOF).

7.1 N-benzyl-2,4-dinitrophenylsulfonamide (1)

$^1H$ NMR (DMSO-d6): δ 9.06-9.04 (t, J=5.8 Hz, 1H), 8.86-8.85 (d, J=2.4 Hz, 1H), 8.52-8.50 (dd, J=8.8, 2.4 Hz, 1H), 8.12-8.10 (d, J=8.4 Hz, 1H), 7.26-7.20 (m, 5H), 4.21-4.19 (d, J=6.0, 2H); 13C NMR (DMSO-d6): δ 149.4, 147.7, 139.6, 135.1, 132.5, 128.7, 128.3, 128.0, 126.7, 120.4, 48.0; FTIR (KBr, cm-1): 3379, 3098, 2345, 1537, 1352, 1161; mp 150-151° C.; HRMS (ESI-TOF) $C_{13}H_{11}N_3O_6S$ $[M+Na]^+$: 360.0266. Found: 360.0275.

7.2 N-(4-chlorobenzyl) 2,4-dinitrophenylsulfonamide (3)

$^1H$ NMR (400 MHz, DMSO-$d_6$): δ 9.06 (s, 1H), 8.87-8.86 (d, J=1.8 Hz, 1H), 8.54-8.52 (dd, J=6.9, 1.8 Hz, 1H), 8.13-8.11 (d, J=6.9 Hz, 1H), 7.33-7.31 (d, J=6.7 Hz, 2H), 7.26-7.25 (d, J=6.7 Hz, 2H), 4.20 (s, 2H); $^{13}C$ NMR (100 MHz, DMSO-$d_6$): δ 149.7, 147.6, 138.4, 136.2, 132.6, 132.0, 130.0, 128.7, 127.5, 120.4, 40.0; FTIR (KBr, $cm^{-1}$): 3385, 3100, 1540, 1346, 1165; mp 161-162° C.; HRMS (ESI-TOF): Calculated $C_{13}H_{10}ClN_3O_6S$ $[M+Na]^+$: 393.9877. Found $[M+Na]^+$: 393.9879.

7.3 N-(4-trifluoromethyl benzyl) 2,4-dinitrophenylsulfonamide (4)

$^1H$ NMR (400 MHz, DMSO-$d_6$): δ 9.15 (s, 1H), 8.85 (s, 1H), 8.50-8.49 (d, J=6.9 Hz, 1H), 8.11-8.10 (d, J=6.8 Hz, 1H), 7.62-7.60 (d, J=6.4 Hz, 2H), 7.47-7.42 (d, J=6.3 Hz, 2H), 4.32 (s, 2H); $^{13}C$ NMR (100 MHz, DMSO-$d_6$): δ 149.7, 147.4, 141.9, 138.4, 128.9, 128.6, 128.3, 127.4, 125.8, 125.5, 121.1, 120.4, 120.3, 46.2; FTIR (KBr, $cm^{-1}$): 3389, 1854, 1354, 1322, 1170, 1120; 176-177° C.; HRMS (ESI-TOF): Calculated $C_{14}H_{10}F_3N_3O_6S$ $[M+Na]^+$: 428.0140. Found $[M+Na]^+$: 428.0136.

7.4 N-(2-trifluoromethyl benzyl) 2,4-dinitrophenylsulfonamide (5)

$^1H$ NMR (400 MHz, DMSO-$d_6$): δ 9.23 (s, 1H), 8.91-8.90 (d, J=2.2 Hz, 1H), 8.60-8.58 (dd, J=8.7, 2.2 Hz, 1H), 8.18-8.16 (d, J=8.6 Hz, 1H), 7.71-7.69 (d, J=7.8 Hz, 1H), 7.65-7.60 (m, 2H), 7.49-7.45 (dd, J=7.8, 2.2 Hz, 1H), 4.39 (s, 2H); $^{13}C$ NMR (100 MHz, DMSO-$d_6$): δ 150.2, 147.9, 138.1, 135.8, 133.2, 131.7, 129.9, 128.5, 127.8, 127.7, 126.8, 126.5, 126.4, 126.3, 126.2, 126.0, 120.6, 43.6; FTIR (KBr, $cm^{-1}$): 3385, 1556, 1540, 1422, 1350, 1313, 1171, 1121, 1104, 1038; mp 157-158° C.; HRMS (ESI-TOF): Calculated $C_{14}H_{10}F_3N_3O_6S$ $[M+Na]^+$: 428.0140. Found $[M+Na]^+$: 428.0141.

7.5 N-(4-methoxyphenyl) 2,4-dinitrophenylsulfonamide (7)

$^1H$ NMR (DMSO-d6) δ 10.70 (s, 1H), 8.88-8.87 (d, J=2.0 Hz, 1H), 8.60-8.57 (dd, J=8.8, 2.0 Hz, 1H), 8.13-8.11 (d, J=8.8 Hz, 1H), 7.05-7.04, (d, J=7.2 Hz, 2H), 6.87-6.85 (d, J=7.2 Hz, 2H), 3.69 (s, 3H); 13C NMR (DMSO-d6) δ 157.9, 150.4, 148.3, 136.8, 132.1, 128.5, 127.6, 125.1, 120.7, 115.1, 56.7; FTIR (KBr, cm-1): 3345, 3098, 2343, 1539, 1357, 1246, 1169, 1029, 907; mp 115-116° C.; HRMS (ESI-TOF) C$_{13}$H$_{11}$N$_3$O$_7$S [M+Na]$^+$: 376.0215. Found: 376.0214.

7.6 N-(2-methoxyphenyl) 2,4-dinitrophenylsulfonamide (8)

$^1$H NMR (400 MHz, DMSO-d$_6$): δ 10.30 (s, 1H), 8.88-8.87 (d, J=2.2 Hz, 1H), 8.62-8.59 (d, J=8.7, 2.3 Hz, 1H), 8.14-8.12 (d, J=8.7 Hz, 1H), 7.26-7.16 (m, 2H), 6.97-6.90 (m, 2H) 3.43 (s, 3H); $^{13}$C NMR (100 MHz, DMSO-d$_6$): δ 154.1, 150.1, 147.7, 138.6, 132.0, 128.9, 128.4, 127.3, 124.0, 121.1, 120.3, 112.5, 55.7; FTIR (KBr, cm$^{-1}$): 3268, 3101, 1605, 1545, 1498, 1410, 1357, 1172, 1132; mp 172-173° C.; HRMS (ESI-TOF): Calculated C$_{13}$H$_{11}$N$_3$O$_7$S [M+Na]$^+$: 376.0215. Found [M+Na]$^+$: 376.0215.

7.7 N-(3-fluorophenyl) 2,4-dinitrophenylsulfonamide (9)

$^1$H NMR (CDCl3): δ 8.68-8.67 (d, J=2.2 Hz, 1H), 8.44-8.42 (dd, J=2.3, 1.8 Hz, 1H), 8.13-8.11 (d, J=8.7 Hz, 1H), 7.35 (s, 1H), 7.29-7.24 (td, J=6.4, 10.1 Hz, 1H), 7.06-7.02 (dt, J=2.2, 9.6 Hz, 1H), 6.97-6.90 (m, 2H); 13C NMR (CDCl3): δ 164.2-161.7 (d, J=248 Hz) 150.1-148.4 (d, J=173 Hz), 137.2, 136.0-135.9 (d, J=9 Hz), 133.5, 131.1-131.0 (d, J=8.58 Hz), 126.9, 120.8, 118.4-118.3 (d, J=11 Hz), 114.2-114.0 (d, J=21 Hz), 110.5-110.3 (d, J=25 S3 Hz); FTIR (KBr, cm-1): 3445, 3267, 3093, 1541, 1354, 1171; mp 172-173° C.; MALDI-TOF MS (m/z): Calculated C12H8FN3O6S [M+Na]$^+$: 379.9452. Found [M+Na]$^+$: 379.9755.

7.8 N-(4-fluorophenyl) 2,4-dinitrophenylsulfonamide (10)

$^1$H NMR (400 MHz, DMSO-d$_6$): δ 11.02 (s, 1H), 8.89 (s, 1H), 8.60-8.58 (d, J=8.6 Hz, 1H), 8.18-8.16 (d, J=8.6 Hz, 1H), 7.16-7.15 (d, J=5.4 Hz, 4H); $^{13}$C NMR (100 MHz, DMSO-d$_6$): δ 161.1, 159.1, 150.5, 148.3, 136.5, 132.4, 132.1, 127.7, 124.8-124.7 (d, J=8 Hz), 120.8, 116.8-116.6 (d, J=22 Hz); FTIR (KBr, cm$^{-1}$): 3299, 1553, 1536, 1348, 1171; mp 127-128° C.; HRMS (ESI-TOF): Calculated C$_{12}$H$_8$FN$_3$O$_6$S [M+K]$^+$: 379.9755. Found [M+K]$^+$: 379.9755.

7.9 N-(4-cyanophenyl) 2,4-dinitrophenylsulfonamide (11)

$^1$H NMR (400 MHz, DMSO-d$_6$): δ 11.79 (s, 1H), 8.93 (s, 1H), 8.61-8.59 (d, J=8.5 Hz, 1H), 8.31-8.29 (d, J=8.6 Hz, 1H), 7.80-7.77 (d, J=8.3 Hz, 2H), 7.28-7.26 (d, J=8.3 Hz, 2H); $^{13}$C NMR (100 MHz, DMSO-d$_6$): δ 150.8, 148.2, 141.3, 136.3, 134.4, 132.2, 128.0, 121.1, 120.1, 119.0, 107.1; FTIR (KBr, cm$^{-1}$): 3252, 2231, 1607, 1555, 1538, 1469, 1346, 1165, 917; mp 186-187° C.; HRMS (ESI-TOF): Calculated C$_{13}$H$_8$N$_4$O$_6$S [M+Na]$^+$: 371.0062. Found [M+Na]$^+$: 371.0062.

7.10 (S) N-(1-phenylethyl)-2,4-dinitrobenzenesulfonamide (12)

$^1$H NMR (400 MHz, DMSO-d$_6$): δ 9.06-9.04 (d, J=7.6 Hz, 1H), 8.79-8.78 (d, J=2.2 Hz, 1H), 8.41-8.38 (dd, J=8.6, 2.2 Hz, 1H), 8.00-7.98 (d, J=8.6 Hz, 1H), 7.23-7.10 (m, 5H), 4.56-4.49 (m, 1H), 1.38-1.36 (d, J=6.9 Hz, 3H); $^{13}$C NMR (100 MHz, DMSO-d$_6$): δ 149.8, 147.6, 142.8, 138.5, 132.1, 128.7, 127.6, 127.1, 126.6, 120.1, 54.0, 23.7; FTIR (KBr, cm$^{-1}$): 3342, 1541, 1442, 1353, 1166; mp 162-163° C.; HRMS (ESI-TOF): Calculated C$_{14}$H$_{13}$N$_3$O$_6$S [M+Na]$^+$: 374.0423. Found [M+Na]$^+$: 374.0422.

7.11 (R) N-(1-phenylethyl)-2,4-dinitrobenzenesulfonamide (13)

$^1$H NMR (400 MHz, DMSO-d$_6$): δ 9.06-9.04 (d, J=8.2 Hz, 1H), 8.79-8.78 (d, J=2.1 Hz, 1H), 8.41-8.38 (dd, J=8.7, 2.1 Hz, 1H), 8.00-7.98 (d, J=8.6 Hz, 1H), 7.23-7.10 (m, 5H), 4.56-4.49 (m, 1H), 1.38-1.36 (d, J=6.9 Hz, 3H); $^{13}$C NMR (100 MHz, DMSO-d$_6$): δ 148.8, 147.6, 142.9, 138.6, 132.1, 128.7, 127.6, 127.2, 126.6, 120.2, 54.0, 23.8; FTIR (KBr, cm$^{-1}$): 3342, 1541, 1442, 1353, 1166; mp 160-161° C.; HRMS (ESI-TOF): Calculated C$_{14}$H$_{13}$N$_3$O$_6$S [M+Na]$^+$: 374.0423. Found [M+Na]$^+$: 374.0424.

7.12 N-(2-phenylethyl) 2,4-dinitrophenylsulfonamide (14)

$^1$H NMR (400 MHz, DMSO-d$_6$): δ 8.85-8.84 (d, J=2.2 Hz, 1H), 8.13-8.11 (d, J=8.7 Hz, 1H), 8.59 (s, 1H), 8.55-8.52 (dd, J=8.7, 2.2 Hz, 1H), 7.31-7.11 (m, 5H), 3.22-3.18 (t, J=7.5, 7.1 Hz, 2H), 2.74-2.71 (t, J=7.4, 7.2 Hz, 2H); $^{13}$C NMR (100 MHz, DMSO-d$_6$): δ 150.0, 147.9, 138.8, 138.2, 131.7, 129.2, 128.8, 127.7, 126.8, 120.5, 44.8, 35.8; FTIR (KBr, cm$^{-1}$): 3348, 1537, 1428, 1342, 1166, 1101; mp 127-128° C.; HRMS (ESI-TOF): Calculated C$_{14}$H$_{13}$N$_3$O$_6$S [M+Na]$^+$: 374.0423. Found [M+Na]$^+$: 374.0423.

7.13 (N-benzyl, N-methyl) 2,4-dinitrophenylsulfonamide (15)

$^1$H NMR (CDCl3): δ 8.50-8.47 (m, 2H), 8.23-8.21 (d, J=9.2 Hz, 1H), 7.36-7.29 (m, 5H), 4.44 (s, 2H), 2.83 (s, 3H); 13C NMR (CDCl3): δ 149.6, 148.1, 138.1, 134.5, 132.7, 128.9, 128.3, 128.2, 126.0, 119.7, 54.2, 34.4; FTIR (KBr, cm-1): 3436, 3105, 2922, 1547, 1357, 1163, 982; mp 132-133° C.; HRMS (ESI-TOF) C$_{14}$H$_{14}$N$_3$O$_6$S [M+H]$^+$: 352.0605. Found: [M+H]$^+$: 352.0603.

7.14 (N-benzyl, N-propyl) 2,4-dinitrophenylsulfonamide (16)

$^1$H NMR (CDCl3): δ 8.47-8.46 (d, J=2.2 Hz, 1H), 8.40-8.37 (dd, J=8.8, 2.4 Hz, 1H), 8.14-8.11 (d, J=8.8 Hz, 1H), 7.32-7.23 (m, 5H), 4.54 (s, 2H), 3.28-3.24 (t, J=8.0, 7.6 Hz, 2H), 1.52-1.43 (m, 2H), 0.79-0.75 (t, J=7.4 Hz, 3H); 13C NMR (CDCl3): δ 149.4, 147.8, 139.6, 135.9, 132.5, 128.7, 128.1, 125.8, 119.6, 51.2, 49.4, 20.9, 10.9; FTIR (KBr, cm-1): 3098, 2927, 1545, 1352, 1155, 1020, 896; mp 120-121° C.; HRMS (ESI-TOF) C$_{16}$H$_{18}$N$_3$O$_6$S [M+H]$^+$: 380.0920. Found: [M+H]$^+$: 380.0916.

7.15 (N-benzyl, N-phenyl) 2,4-dinitrophenylsulfonamide (17)

$^1$H NMR (400 MHz, DMSO-d$_6$): δ 9.02-9.01 (d, J=2.2 Hz, 1H), 8.55-8.52 (dd, J=8.7, 2.3 Hz, 1H), 8.00-7.98 (d, J=8.7 Hz, 1H), 7.31-7.14 (m, 10H), 4.95 (s, 2H); $^{13}$C NMR (100 MHz, DMSO-d$_6$): δ 150.7, 148.1, 132.9, 129.8, 129.5, 129.1, 129.0, 128.7, 128.3, 127.2, 120.5, 55.4; FTIR (KBr, cm$^{-1}$): 1604, 1550, 1536, 1351, 1169, 1106; mp 134-135° C.; HRMS (ESI-TOF): Calculated C$_{19}$H$_{15}$N$_3$O$_6$S [M+Na]$^+$: 436.0579. Found [M+Na]$^+$: 436.0578.

7.16 (N-methyl, N-phenyl) 2,4-dinitrophenylsulfonamide (18)

$^1$H NMR (400 MHz, DMSO-d$_6$): δ 9.00-8.99 (d, J=2.2 Hz, 1H), 8.54-8.51 (d, J=8.7, 2.2 Hz, 1H), 7.90-7.87 (d, J=8.7 Hz, 1H), 7.42-7.38 (m, 3H), 7.26-7.24 (m, 2H), 3.3 (s, 3H); $^{13}$C NMR (100 MHz, DMSO-d$_6$): δ 150.7, 148.3, 140.1, 134.5, 132.7, 129.9, 128.8, 127.6, 127.2, 127.1, 120.5; FTIR (KBr, cm$^{-1}$): 1556, 1541, 1365, 1184, 1061; mp 156-157° C.; HRMS (ESI-TOF): Calculated C$_{13}$H$_{11}$N$_3$O$_6$S [M+Na]$^+$: 360.0266. Found [M+Na]$^+$: 360.0266.

7.17 N-methyl, N-(2-phenylethyl) 2,4-dinitrophenylsulfonamide (19)

$^1$H NMR (400 MHz, CDCl$_3$): δ 8.40 (s, 1H), 8.38-8.36 (d, J=6.9 Hz, 1H), 8.06-8.04 (d, J=6.8 Hz, 1H), 7.24-7.15 (m, 5H), 3.55-3.52 (t, J=6, 5.7 Hz, 2H), 2.99 (s, 3H), 2.92-2.89 (t, J=5.8, 5.7 Hz, 2H); $^{13}$C NMR (100 MHz, CDCl$_3$): δ 149.5, 147.9, 138.3, 137.7, 132.4, 128.9, 128.7, 126.9, 126.1, 119.7, 55.1, 35.0, 34.5; FTIR (KBr, cm$^{-1}$): 1552, 1537, 1352, 1163, 965; sticky oil, HRMS (ESI-TOF): Calculated C$_{15}$H$_{15}$N$_3$O$_6$S [M+Na]$^+$: 388.0579. Found [M+Na]$^+$: 388.0579.

7.18 N-benzyl, N-(2-phenylethyl) 2,4-dinitrophenylsulfonamide (20)

$^1$H NMR (400 MHz, DMSO-d$_6$): δ 8.94-8.93 (d, J=2.2 Hz, 1H), 8.47-8.44 (dd, J=8.8, 2.3 Hz, 1H), 8.26-8.24 (d, J=8.7 Hz, 1H), 7.39-7.33 (m, 5H), 7.19-7.02 (m, 5H), 4.62 (s, 2H), 3.42-3.33 (t, J=8.1, 7.6 Hz, 2H), 2.63-2.60 (t, J=7.9, 7.6 Hz, 2H); $^{13}$C NMR (100 MHz, DMSO-d$_6$): δ 150.4, 147.7, 138.31, 137.2, 136.2, 132.2, 129.2, 129.1, 128.9, 128.8, 128.5, 127.5, 126.9, 120.6, 51.4, 49.3, 34.2 FTIR (KBr, cm$^{-1}$): 1543, 1370, 1347, 1158; mp 111-112° C.; HRMS (ESI-TOF): Calculated C$_{21}$H$_{19}$N$_3$O$_6$S [M+Na]$^+$: 464.0892. Found [M+Na]$^+$: 464.0893.

7.19 Methyl 2-{[(2,4-dinitrophenyl)sulfonyl]amino}propanoate (21)

$^1$H NMR (400 MHz, CDCl$_3$): δ 8.76-8.75 (d, J=2.1 Hz, 1H), 8.55-8.52 (dd, J=8.6, 2.2 Hz, 1H), 8.30-8.28 (d, J=8.6 Hz, 1H), 4.36-4.28 (m, 1H), 3.59 (s, 3H), 1.54-1.52 (d, J=7.2 Hz, 3H); $^{13}$C NMR (100 MHz, CDCl$_3$): δ 172.0, 149.8, 147.9, 139.9, 132.1, 127.2, 121.1, 52.9, 29.1, 19.5; HRMS (ESI-TOF): Calculated C$_{10}$H$_{11}$N$_3$O$_8$S [M+Na]$^+$: 356.0165. Found [M+Na]$^+$: 356.0164.

7.20 Methyl 1-[(2,4-dinitrophenyl)sulfonyl]pyrrolidine-2-carboxylate (22)

$^1$H NMR (500 MHz) δ 8.51-8.46 (m, 2H), 8.33-8.31 (d, J=8.5 Hz, 1H), 4.64-4.62 (m, 1H), 3.68 (s, 3H), 3.65-3.64 (d, J=6.0 Hz, 1H), 2.36-2.29 (m, 1H), 2.12-2.01 (m, 3H); 13C NMR (125 MHz) δ 171.9, 149.6, 148.1, 138.5, 132.7, 126.0, 119.5, 61.3, 52.6, 49.0, 31.0, 24.5; FTIR (KBr, cm$^{-1}$): 1740, 1537, 1352, 1210, 1161. as sticky oil, HRMS (ESI-TOF): Calculated C$_{12}$H$_{13}$N$_3$O$_8$S [M+Na]$^+$: 382.0316. Found [M+Na]$^+$: 382.0312.

7.21 4-[(2,4-dinitrophenyl)sulfonyl]morpholine (23)

$^1$H NMR (500 MHz, CDCl3) δ 8.51 (dd, J=8.0, 2.5 Hz, 1H), 8.47 (d, J=2.0 Hz, 1H), 8.19 (d, J=8.5 Hz, 1H), 3.75 (t, J=5.0 Hz, 4H), 3.33 (t, J=5.0 Hz, 4H); $^{13}$C NMR (125 MHz, CDCl3): δ 149.9, 14.8, 136.7, 132.7, 126.1, 119.8, 66.4, 46.1; mp 144-145° C.; HRMS (ESI-TOF): Calculated C$_{10}$H$_{11}$N$_3$O$_7$SNa [M+Na]$^+$: 340.0215. Found [M+Na]$^+$: 340.0218.

7.22 1-[(2,4-dinitrophenyl)sulfonyl]piperidine (24)

$^1$H NMR (400 MHz, CDCl$_3$): δ 8.48 (dd, J=9.0, 1.8 Hz, 1H), 8.43 (d, J=2.4 Hz, 1H), 8.19 (d, J=8.8 Hz, 1H) 3.30 (t, J=5.4 Hz, 4H), 1.66 (m, 4H), 1.57 (m, 2H); 13C NMR (100 MHz, CDCl3): δ 149.8, 148.4, 137.8, 132.7, 126.2, 119.8, 47.2, 25.6, 23.6; mp 138-138° C.; HRMS (ESI-TOF): Calculated C$_{11}$H$_{13}$N$_3$O$_6$S [M+Na]$^+$: 338.0423. Found [M+Na]$^+$: 338.0442.

7.23 1-[(2,4-dinitrophenyl)sulfonyl]-4-methylpiperazine (25)

$^1$H NMR (CDCl3): δ 8.51-8.46 (m, 2H), 8.21-8.18 (d, J=8.8 Hz, 1H), 3.39-3.36 (t, J=5.2, 4.8 Hz, 4H), 2.50-2.48 (t, J=5.2, 4.8 Hz, 4H), 2.31 (s, 3H); $^{13}$C NMR (CDCl3): δ 149.7, 148.3, 137.2, 132.5, 126.0, 119.7, 54.3, 46.0, 45.8; S2 FTIR (KBr, cm$^{-1}$): 3437, 3108, 2943, 2842, 2803, 1545, 1361, 1169, 957; mp 164-165° C.; HRMS (ESI-TOF): Calculated C11H15N4O6S [M+H]$^+$: 331.0712. Found [M+H]$^+$: 331.0714.

7.24 N,N-diallyl-2,4-dinitrobenzenesulfonamide (32)

$^1$H NMR (400 MHz, DMSO-d$_6$): δ 8.98-8.97 (d, J=1.7 Hz, 1H), 8.57-8.55 (dd, J=6.9, 1.7 Hz, 1H), 8.36-8.34 (d, J=7.0 Hz, 1H), 5.71-5.63 (m, 2H), 5.20-5.18 (t, J=9.3 Hz, 4H), 3.92-3.91 (d, J=4.8 Hz, 4H); $^{13}$C NMR (100 MHz, DMSO-d$_6$): δ 150.5, 147.8, 137.3, 132.6, 132.5, 127.5, 120.6, 120.0, 49.8. FTIR (KBr, cm$^{-1}$): 1557, 1538, 1343, 1154, 1095; mp 105-106° C.; HRMS (ESI-TOF): Calculated C$_{12}$H$_{13}$N$_3$O$_6$S [M+Na]$^+$: 350.0423. Found [M+Na]$^+$: 350.0423.

7.25 N-benzyl-2,4-dinitro-N-prop-2-yn-1-ylbenzenesulfonamide (33)

$^1$H NMR (400 MHz, DMSO-d$_6$): δ 9.02 (s, 1H), 8.62-8.59 (d, J=8.2 Hz, 1H), 8.43-8.41 (d, J=8.6 Hz, 1H), 7.39-7.30 (m, 5H), 4.56 (s, 1H), 4.0 (s, 1H), 3.26 (s, 1H); $^{13}$C NMR (100 MHz, DMSO-d$_6$): δ 150.7, 148.2, 136.2, 134.9, 132.8, 129.3, 128.7, 127.3, 120.6, 120.5, 77.8, 76.6, 51.0, 36.8; FTIR (KBr, cm$^{-1}$): 1602, 1345, 1158, 1115, 1063; mp 91-92° C.; HRMS (ESI-TOF): Calculated C$_{16}$H$_{13}$N$_3$O$_6$S [M+Na]$^+$: 375.0525. Found [M+Na]$^+$: 375.0524.

7.26 N,N'-(propane-1,3-diyl)bis(N-benzyl-2,4-dinitrobenzenesulfonamide) (34)

White solid (18 mg, 15.38%): mp 186-189° C.; IR (v$_{max}$, cm$^{-1}$): 3444, 3104, 1561, 1531, 1371, 1166, 901, 747; $^1$H NMR (400 MHz, DMSO): 8.96 (d, J=2.2 Hz, 2H), 8.51 (dd, J=2.2, 8.72 Hz, 2H), 8.21 (d, J=8.72 Hz, 2H), 7.32 (m, 2H), 7.16 (m, 4H), 4.37 (S, 4H) 3.05 (t, J=7.36 Hz, 4H) 1.43 (Q, J=6.72, 2H); $^{13}$C NMR (100 MHz, DMSO): 150, 147, 136, 135, 132, 129, 128, 127, 120, 51, 45, 26; HRMS (MALDI) for [C$_{29}$H$_{26}$N$_6$O$_{12}$S$_2$+Na$^+$]: calcd., 737.106. Found: 737.1230.

7.27 N-benzyl-N-(3-(N-(3-methoxyphenyl)-2,4-dinitrophenylsulfonamido)propyl)-2,4-dinitrobenzenesulfonamide (36)

White solid (42 mg, 33%): mp 108-110° C.; IR (v$_{max}$, cm$^{-1}$): 3104, 2360, 1604, 1537, 1369, 1164, 1024, 966, 746, 696, 607; $^1$H NMR (400 MHz, DMSO): 8.97 (d, J=2.2 Hz, 1H), 8.94 (d, J=11.6 Hz, 1H), 8.52 (dd, J=2.1, 8.8 Hz, 1H), 8.49 (dd, J=2.4, 8.9 Hz, 1H), 8.28 (d, J=8.72 Hz, 1H), 7.83 (d, J=8.72 Hz, 1H), 7.25 (m, 6H), 6.95 (d, J=8.64 Hz, 1H), 6.64 (s, 1H), 6.59 (d, J=8.2, 1H), 4.49 (s, 2H), 3.69 (s, 3H), 3.60 (t, J=6.4 Hz, 2H), 3.30 (t, J=8.2 Hz, 2H), 1.43 (Q, J=7.6 Hz, 2H); $^{13}$C NMR (100 MHz, DMSO): 160.22, 150.68, 150.44, 148.07, 147.96, 137.95, 137.09, 136.30, 134.94, 132.83, 132.13, 130.69, 129.15, 128.40, 127.52, 127.12, 121.29, 120.71, 120.45, 55.85, 52.07, 49.35, 46.10, 27.57; MALDI for [$C_{29}H_{26}N_6O_{13}S_2$+Na$^+$]: calcd., 753.0896 Found: 753.0326.

7.28 N-benzyl-N-(3-(N-(4-methoxyphenyl)-2,4-dinitrophenylsulfonamido)propyl)-2,4-di nitrobenzenesulfonamide (37)

White solid (45 mg, 33%): mp 118-120° C.; IR ($v_{max}$, cm$^{-1}$): 3107, 1605, 1537, 1508, 1351, 1303, 1163, 1033, 833, 745; $^1$H NMR (400 MHz, DMSO): 8.98 (d, J=1.8 Hz, 1H), 8.94 (d, J=1.6 Hz, 1H), 8.52 (dd, J=1.96, 8.7 Hz, 1H), 8.47 (dd, J=1.8, 8.6 Hz, 1H), 8.29 (d, J=8.6 Hz, 1H), 7.76 (d, J=8.7 Hz, 1H), 7.31 (m, 5H), 6.92 (d, J=8.9 Hz, 2H), 6.86 (d, 8.7 Hz, 2H), 4.5 (s, 2H), 3.77 (s, 3H), 3.55 (t, J=5.4 Hz, 2H), 3.29 (t, J=7.8 Hz, 2H), 1.39 (Q, J=6.96 Hz, 2H); $^{13}$C NMR (100 MHz, DMSO): 159.57, 150.62, 150.44, 148.02, 147.99, 137.09, 136.26, 135.24, 132.86, 132.14, 130.75, 129.19, 129.03, 128.41, 127.54, 127.08, 120.72, 120.42, 115.14, 55.90, 52.07, 49.67, 46.05, 27.07; MALDI for [$C_{29}H_{26}N_6O_{13}S_2$+K$^+$]: calcd., 769.1979 Found: 769.0140.

7.29 N-benzyl-N-(3-(2,4-dinitro-(N-phenyl) phenylsulfonamido)propyl)-2,4 dinitro benzene sulfonamide (38)

White solid (24 mg, 17%): mp 151-153° C.; IR ($v_{max}$, cm$^{-1}$): 3106, 1552, 1347, 1164, 747, 607; $^1$H NMR (400 MHz, CDCl$_3$): 8.48-8.42 (m, 3H), 8.24-8.18 (m, 2H), 7.60 (d, J=8.68 Hz, 1H), 7.20-7.37 (m, 8H), 4.51 (s, 2H), 3.68 (t, J=8.68 Hz, 2H), 3.37 (t, J=7.5 Hz, 2H), 1.61 (Q, J=7.8 Hz, 2H); $^{13}$C NMR (100 MHz, CDCl$_3$): 149.79, 149.73, 147.95, 138.80, 137.05, 136.68, 134.83, 133.85, 132.82, 130, 129.40, 129.34, 129.02, 128.33, 126.35, 125.54, 119.97, 52.18, 50.36, 45.39, 27.35; MALDI for [$C_{28}H_{24}N_6O_{12}S_2$+K$^+$]: calcd., 739.1877 Found: 739.07.

7.30 N-benzyl-N-(3-(N-(2-fluorophenyl)-2,4-dinitrophenylsulfonamido)propyl)-2,4-dinitrobenzenesulfonamide (39)

White solid (26 mg, 14%): mp 151-153° C.; IR ($v_{max}$, cm$^{-1}$): 3105, 1546, 1356, 1166, 1369, 744, 605; $^1$H NMR (400 MHz, DMSO): 8.97 (s, 2H), 8.53 (d, J=8.4 Hz, 2H), 8.29 (dd, J=8.56 Hz, 1H), 7.96 (d, J=8.68 Hz, 1H), 7.47 (s, 1H), 7.25 (m, 7H), 7.11 (d, J=7.1, 1H), 4.48 (s, 2H), 3.55 (s, J=5.8 Hz, 2H), 3.31 (t, J=7.7 Hz, 2H), 1.41 (Q, J=5.7 Hz, 2H); $^{13}$C NMR (100 MHz, DMSO): 150.79, 150.47, 147.95, 137.05, 136.26, 135.44, 132.72, 132.63, 131.50, 129.17, 128.45, 128.35, 127.56, 127.30, 125.77, 124.09, 123.97, 120.71, 120.46, 117.53, 117.33, 52.18, 49.35, 46.12, 27.44; MALDI for [$C_{28}H_{23}FN_6O_{13}S_2$+K$^+$]: calcd., 757.1782 Found: 756.9796.

7.31 N-benzyl-N-(3-(N-benzyl-2-nitrophenylsulfonamido)propyl)-2,4-dinitrobenzenesulfon amide (40)

White solid (62 mg, 30%): mp 159-167° C.; IR ($v_{max}$, cm$^{-1}$): 1358, 1442, 1350, 1169, 898, 783, 602; $^1$H NMR (400 MHz, DMSO): 8.96 (s, 1H), 8.52 (d, J=8.1 Hz, 1H), 8.21 (d, J=8 Hz, 1H), 7.89 (m, 4H), 7.31 (m, 6H), 7.16 (m, 4H), 4.37 (s, 2H), 4.35 (s, 2H), 3.25 (s, 2H), 3.02 (s, 4H), 1.43 (s, 2H); $^{13}$C NMR (100 MHz, DMSO): 150.42, 147.82, 137, 136.39, 135.95, 135.18, 133.05, 132.17, 132.08, 130.32, 129.22, 129.10, 128.43, 128.37, 128.30, 127.52, 124.54, 120.70, 51.41, 51.23, 45.46, 45.19, 26.50; MALDI for [$C_{29}H_{27}N_5O_{10}S_2$+K$^+$]: calcd., 708.2182 Found: 708.0237.

7.32 N-benzyl-N-(3-(N-benzyl-3-nitrophenylsulfonamido)propyl)-2,4-dinitrobenzenesulfon amide (41)

White solid (77 mg, 36%): mp 140-142° C.; IR ($v_{max}$, cm$^{-1}$): 3114, 1554, 1350, 1535, 1360, 1168, 896, 785, 572; $^1$H NMR (400 MHz, CDCl$_3$): 8.55 (s, 1H), 8.43 (m, 2H), 8.36 (dd, J=1.9, 8.68 Hz, 1H), 8.05 (m, 2H), 7.72 (t, J=8 Hz, 1H), 7.27 (broad, 6H), 7.14 (m, 4H) 4.35 (s, 2H), 4.25 (s, 2H), 3.25 (s, 2H), 3.17 (t, J=7.2 Hz, 2H), 3.05 (t, J=7.3 Hz, 2H), 1.60 (Q, J=7.3 Hz, 2H); $^{13}$C NMR (100 MHz, DMSO): 150.41, 148.46, 147.83, 141.12, 137.06, 136.58, 136.06, 133.25, 132.25, 132.19, 132.06, 129.19, 128.99, 128.55, 128.39, 128.19, 127.99, 127.49, 122, 120.66, 51.89, 51.50, 46.13, 45.72, 40.62, 27.01; MALDI for [$C_{29}H_{27}N_5O_{10}S_2$+K$^+$]: calcd., 708.2182 Found: 708.0481.

7.33 N-benzyl-N-(3-(N-benzyl-4-nitrophenylsulfonamido)propyl)-2,4-dinitrobenzenesulfon amide (42)

White solid (43 mg, 21%): mp 171-173° C.; $^1$H NMR (400 MHz, DMSO): 8.97 (d, J=2.1 Hz, 1H), 8.51 (dd, J=2.1, 8.68 Hz, 1H), 8.37 (d, J=8.7 Hz, 2H), 8.21 (m, 2H), 7.30 (m, 6H), 7.16 (t, J=2.1 Hz, 4H), 4.35 (s, 2H), 4.23 (s, 2H), 3.03 (t, J=7.4 Hz, 2H), 2.92 (t, J=7.3 Hz, 2H), 1.35 (Q, J=7 Hz, 2H); $^{13}$C NMR (100 MHz, DMSO): 150.41, 150.26, 147.82, 144.94, 137.02, 136.61, 136.03, 132.19, 129.19, 129.04, 128.94, 128.52, 128.32, 128.25, 127.49, 125.49, 125.20, 120.66, 51.91, 51.42, 45.98, 45.64, 26.93.

We claim:

1. A pharmaceutical composition for the treatment of an infection by at least one pathogen of the genus *Staphylococcus*, *Enterococcus* or *Mycobacterium*, comprising an effective amount of a thiol activated prodrug of SO$_2$ having general Formula I or a pharmaceutically acceptable salt thereof, exhibiting tunable release profiles of SO$_2$ with therapeutic efficacy against said infection,

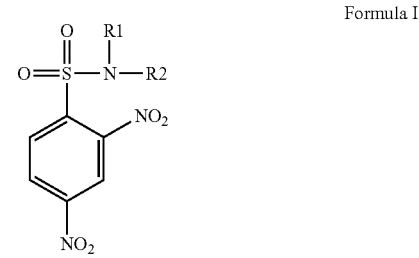

Formula I wherein either:
  a) R1 is independently selected from the group consisting of H, (C1-C8) alkyl, alkylaryl, allyl, (C2-C8) alkynyl, a group of Formula II and a group of Formula III; and

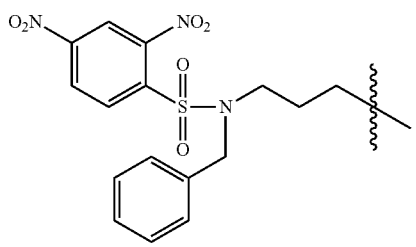

Formula II

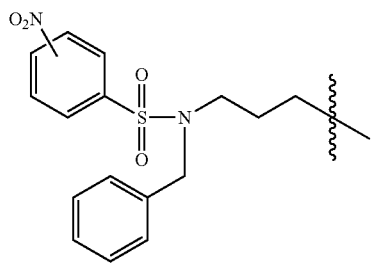

Formula III

R2 is selected from the group consisting of allyl, a group of Formula IV and a group of Formula V;

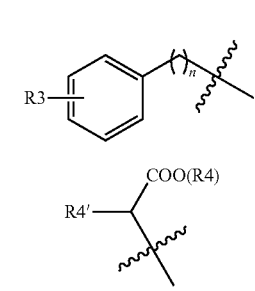

Formula IV

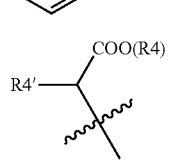

Formula V wherein n is either 0 or 1; R3 is independently selected from the group consisting of H, halogen, —CF3, (C1-C6) alkoxy, and —CN; and R4 and R4' are independently selected from the group consisting of and substituted or unsubstituted (C1-C6) alkyl; or b) R1 and R2, together with the nitrogen atom to which R1 and R2 are attached, form a 5 or 6 membered heterocyclic ring, optionally containing an additional substituted or unsubstituted heteroatom selected from the group consisting of O and N, said 5 or 6 membered heterocyclic ring being optionally substituted with a substituent selected from the group consisting of H, (C1-C6) alkyl, and —COO(R5);

wherein R5 is H or (C1-C6) alkyl;

further comprising an active ingredient selected from the group consisting of anti-tuberculosis drugs selected from the group consisting of rifampin, isoniazide, ethambutol, and pyrazinamide; Fluoroquinolones; Cephalosporins; Penicillins; Carbepenems; Aminoglycosides; Tetracyclines; and mixtures thereof.

2. The pharmaceutical composition according to claim 1, wherein the infection is caused by Mycobacterial tuberculosis.

3. The pharmaceutical composition according to claim 1, wherein the infection is caused by a pathogen selected from the group consisting of *Staphylococcus aureus* and *Entervococcus faecalis*.

4. The pharmaceutical composition for the treatment of an infection by at least one pathogen of the genus *Staphylococcus, Enterococcus* or *Mycobacterium* according to claim 1, further comprising a pharmaceutically acceptable excipient, a pharmaceutically acceptable vehicle, or a mixture thereof.

5. A pharmaceutical composition for the treatment of an infection by at least one pathogen of the genus *Staphylococcus, Enterococcus* or *Mycobacterium*, comprising an effective amount of a thiol activated prodrug of $SO_2$ selected from the group consisting of:

i. N-(4-chlorobenzyl) 2,4-dinitrophenylsulfonamide (3);
ii. N-(4-trifluoromethyl benzyl) 2,4-dinitrophenylsulfonamide (4);
iii. N-(2-trifluoromethyl benzyl) 2,4-dinitrophenylsulfonamide (5);
iv. N-(2-methoxyphenyl) 2,4-dinitrophenylsulfonamide (8);
v. N-(3-fluorophenyl) 2,4-dinitrophenylsulfonamide (9);
vi. N-(4-cyanophenyl) 2,4-dinitrophenylsulfonamide (11);
vii. (S)N-(1-phenylethyl)-2,4-dinitrobenzenesulfonamide (12);
viii. (R)N-(1-phenylethyl)-2,4-dinitrobenzenesulfonamide (13);
ix. N-(2-phenylethyl) 2,4-dinitrophenylsulfonamide (14);
x. (N-benzyl, N-propyl) 2,4-dinitrophenylsulfonamide (16);
xi. (N-benzyl, N-phenyl) 2,4-dinitrophenylsulfonamide (17);
xii. N-methyl, N-(2-phenylethyl) 2,4-dinitrophenylsulfonamide (19);
xiii. N-benzyl, N-(2-phenylethyl) 2,4-dinitrophenylsulfonamide (20);
xiv. Methyl 2-{[(2,4-dinitrophenyl)sulfonyl]amino}propanoate (21);
xv. methyl 1-[(2,4-dinitrophenyl)sulfonyl]pyrrolidine-2-carboxylate (22);
xvi. 1-[(2,4-dinitrophenyl)sulfonyl]-4-methylpiperazine (25);
xvii. N,N-diallyl-2,4-dinitrobenzenesulfonamide (32);
xviii. N-benzyl-2,4-dinitro-N-prop-2-yn-1-ylbenzenesulfonamide (33);
xix. N,N'-(propane-1,3-diyl)bis(N-benzyl-2,4-dinitrobenzenesulfonamide) (34);
xx. N-benzyl-N-(3-(N-(2-methoxyphenyl)-2,4-dinitrophenylsulfonamido)propyl)-2,4-dinitrobenzenesulfonamide (35);
xxi. N-benzyl-N-(3-(N-(3-methoxyphenyl)-2,4-dinitrophenylsulfonamido)propyl)-2,4 dinitrobenzenesulfonamide (36);
xxii. N-benzyl-N-(3-(N-(4-methoxyphenyl)-2,4-dinitrophenylsulfonamido)propyl)-2,4-dinitrobenzenesulfonamide (37);
xxiii. N-benzyl-N-(3-(2,4-dinitro-(N-phenyl) phenylsulfonamido)propyl)-2,4 dinitro benzene sulfonamide (38);
xxiv. N-benzyl-N-(3-(N-(2-fluorophenyl)-2,4-dinitrophenylsulfonamido)propyl)-2,4-dinitrobenzenesulfonamide (39);
xxv. N-benzyl-N-(3-(N-benzyl-2-nitrophenylsulfonamido)propyl)-2,4-dinitrobenzenesulfon-amide (40);
xxvi. N-benzyl-N-(3-(N-benzyl-3-nitrophenylsulfonamido)propyl)-2,4-dinitrobenzenesulfon-amide (41); and
xxvii. N-benzyl-N-(3-(N-benzyl-4-nitrophenylsulfonamido)propyl)-2,4-dinitrobenzenesulfonamide (42);

said pharmaceutical composition further comprising an active ingredient selected from the group consisting of anti-tuberculosis drugs selected from the group consisting of rifampin, isoniazids, ethambutol, and pyrazinamide; Fluroquinolones; Cephalosporins; Penicillins; Carbepenems; Aminoglycosides; Tetracyclines; and mixtures thereof.

6. A pharmaceutical composition according to claim 5, further comprising a pharmaceutically acceptable excipient, a pharmaceutically acceptable vehicle, or a mixture thereof.

7. A method of treating or inhibiting growth of an infection by at least one pathogen of the genus *Staphylococcus, Enterococcus* or *Mycobacterium* in a subject comprising administering to the subject a pharmaceutical composition according to claim 1, said pharmaceutical composition further comprising a pharmaceutically acceptable excipient, a pharmaceutically acceptable vehicle, or a mixture thereof.

8. The method of treating or inhibiting growth of an infection according to claim 7, further comprising administering at least one additional active ingredient.

9. The method of treating or inhibiting growth of an infection according to claim 7, wherein, the infection is caused by Mycobacterial tuberculosis.

10. The method of treating or inhibiting growth of an infection according to claim 8, wherein, the infection is caused by Mycobacterial tuberculosis.

11. The method according to claim 7, wherein the subject is a mammal.

12. A method of treating or inhibiting growth of an infection by at least one pathogen of the genus *Staphylococcus, Enterococcus* or *Mycobacterium* in a subject comprising administering to the subject a pharmaceutical composition according to claim 5, together with a pharmaceutically acceptable excipient, a pharmaceutically acceptable vehicle, or a mixture thereof.

13. The method of treating or inhibiting growth of an infection according to claim 12, wherein the infection is caused by a pathogen selected from the group consisting of *Staphylococcus aureus* and *Enterococcus faecalis*.

14. The method of treating or inhibiting growth of an infection according to claim 12, wherein the infection is caused by Mycobacterial tuberculosis.

15. The method of treating or inhibiting growth of a bacterial infection according to claim 12, wherein the subject is a mammal.

* * * * *